(12) United States Patent
Bennett et al.

(10) Patent No.: US 10,696,983 B2
(45) Date of Patent: Jun. 30, 2020

(54) METHOD FOR TRANSDUCING CELLS WITH PRIMARY CILIA

(75) Inventors: Jean Bennett, Bryn Mawr, PA (US); Joshua Lipschutz, Bala Cynwyd, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 1088 days.

(21) Appl. No.: 12/601,898

(22) PCT Filed: May 30, 2008

(86) PCT No.: PCT/US2008/006873
§ 371 (c)(1),
(2), (4) Date: Aug. 9, 2010

(87) PCT Pub. No.: WO2008/150459
PCT Pub. Date: Dec. 11, 2008

(65) Prior Publication Data
US 2010/0297084 A1   Nov. 25, 2010

Related U.S. Application Data

(60) Provisional application No. 60/924,755, filed on May 30, 2007.

(51) Int. Cl.
*C12N 15/86* (2006.01)
*A61K 48/00* (2006.01)

(52) U.S. Cl.
CPC .............. *C12N 15/86* (2013.01); *A61K 48/00* (2013.01); *C12N 2750/14143* (2013.01)

(58) Field of Classification Search
CPC .................................................. C12N 15/86
See application file for complete search history.

(56) References Cited

U.S. PATENT DOCUMENTS

2004/0208847 A1   10/2004   Rolling et al.
2006/0110761 A1   5/2006   Sheffield et al.

FOREIGN PATENT DOCUMENTS

WO    WO 01/090307 A3    11/2001

OTHER PUBLICATIONS

Chen et al., IDS Nov. 25, 2009.*
Stieger et al., 2006, Molecular Therapy, vol. 13(5), pp. 967-975.*
Boycott et al., 1984, J. Cell Science, vol. 66, pp. 95-118.*
Weber et al. (2003, Molecular Therapy, vol. 7(6), pp. 774-781).*
Dinculescu et al. (2005, Human Gene Therapy, vol. 16, pp. 649-663).*
Maminishkis et al. (2006, IOVS, vol. 47(8), pp. 3612-3624).*
Tenenbaum et al., 2003, Current Gene Therapy, vol. 3, pp. 545-565).*
Vandenberghe et al. (2012, Gene Therapy, vol. 19, pp. 162-168).*
Douglas et al., 1996, Nature Biot., vol. 14, pp. 1574-1578.*
Marmorstein et al. (2002, PNAS, vol. 99(20), pp. 13067-13072).*
Balakrishnan et al. (2014, Current Gene Therapy, vol. 14, pp. 1-15).*
Shen et al. (2012, J. Virology, vol. 86(19), pp. 10408-10417).*
Singhal et al. (2005, Indian J. Ophtthalmol., vol. 53, pp. 109-113) (Year: 2005).*
Chen et al. Gene Delivery in Renal Tubular Epithelial Cells Using Recombinant Adeno-associated Viral Vectors. J AM Soc Nephrol 2003, vol. 14, pp. 947-958: Abstract Fig 1A: p. 955, para 1; p. 956, para 3.
Auricchio et al. Exchange of surface proteins impacts on viral vector cellular specificity and transduction characteristics: the retina as a model Human Molecular Genetics, 2001, vol. 10, No. 26 3075-3081.
Bedrosian et al. In vivo delivery of recombinant viruses to the fetal murine cochlea: transduction characteristics and long-term effects on auditory function. Molecular Therapy Sep. 2006, vol. 14, No. 3, pp. 328-335.
Ong et al. Polycystic kidney disease—the ciliary connection. the Lancet, Mar. 1, 2003, vol. 361, No. 9359, pp. 774-776: p. 774, para 2.
Chiang-Ting et al. Adenovirus-Mediated bcl-2 Gene Transfer Inhibits Renal Ischemia/Reperfusion Induced Tubular Oxidative Stress and Apoptosis American Journal of Transplantation vol. 5 Issue 6, pp. 1194-1203 Published Online: Feb. 25, 2005.
Keiser et al. 135. AAV-Mediated Gene Delivery to Evaluate the Biology of an Inherited Macular Degeneration. Molecular Therapy May 2005, vol. 11, supp 1, pp. S54-S55; Abstract.
Bennett et al., "Stable transgene expression in rod photoreceptors after recombinant adeno-associated virus-mediated gene transfer to monkey retina", PNAS, vol. 96, pp. 9920-9925, Aug. 1999.
Varki, "N-glycolylneuraminic acid deficiency in humans", Biochimie 83 (2001) 615-622.

* cited by examiner

*Primary Examiner* — Thaian N. Ton
*Assistant Examiner* — David A. Montanari
(74) *Attorney, Agent, or Firm* — Mark S. Cohen; Pearl Cohen Zedek Latzer Baratz LLP

(57) ABSTRACT

This invention provides methods for transducing a ciliated cell with a recombinant serotype 2 adeno-associated virus (AAV) vector. Additionally, the invention provides methods of treating diseases associated with a mutated gene by transducing a ciliated cell with a recombinant serotype 2 AAV vector containing a corrective transgene.

38 Claims, 10 Drawing Sheets

METHOD FOR TRANSDUCING CELLS WITH PRIMARY CILIA

CROSS-REFERENCE TO RELATED APPLICATIONS

This is a national phase application of PCT international application PCT/US08/06873, filed May 30, 2008, claiming priority to U.S. provisional patent application 60/924,755, filed May 30, 2007, which is incorporated by reference herein in its entirety.

FIELD OF INVENTION

This invention provides methods for transducing primary ciliated cells with an AAV vectors.

BACKGROUND OF THE INVENTION

Kidney disease can be caused by a variety of insults, ranging from inherited gene defects, damage caused by disease of other organ systems (such as diabetes, immune disorders), infections, or exposure to toxic chemicals. Kidney disease can be secondary to other systemic diseases, such as hemolytic uremic syndrome, Lupus nephritis, or high blood pressure. Inherited kidney disease can be caused by mutations in genes expressed by renal tubular epithelial cells, the cells which line the collecting ducts of the kidney. Mutations that affect these cells cause cellular dysfunction, disorganization and death of these cells with resultant cyst formation. Such diseases are common potentially lethal genetic disorders in humans. Poly cystic kidney disease (PKD) is an example of such diseases and is one of the most common inherited diseases in humans. Twenty million Americans (1 in 9 adults) have chronic kidney disease. Autosomal dominant PKD (ADPKD) affects between 1/500 and 1/1000 people, or 500,000 Americans alone, and results in cystic and tubular overgrowth that leads to destruction of the normal kidney architecture and renal failure Mutations in PKD1 account for 85% of the cases of ADPKD; mutations in PKD2 account for the remaining 15% of ADPKD. The latter disease affects 75,000 Americans.

There are no treatments available for PKD and many other chronic kidney diseases. People with such diseases feel fatigued, develop high blood pressure and anemia, and often suffer from pain and weak bones. When kidney disease progresses to kidney failure, individuals require dialysis or kidney transplant in order to survive. While some experimental reagents are in early stage clinical trials, the mainstay of treatment, especially for ADPKD, is supportive care. Ultimately, individuals with end-stage kidney disease must go on dialysis or receive a kidney transplant.

The rare inherited macular degeneration Malattia Leventinese (ML), also known as Doyne honeycomb retinal dystrophy (DHRD), is an autosomal dominant disorder characterized by the formation of deposits called drusen between the retinal pigment epithelium (RPE) and Bruch's membrane by middle age. During the latter stages of the disease, pathology, such as decreased visual acuity, geographic atrophy, pigmentary changes, and choroidal neovascularization can become apparent. The characteristics of ML have much in common with age-related macular degeneration (AMD), a heterogeneous disorder which is the leading cause of blindness in the elderly in the developed part of the world (4, 5), affecting more than 20% of the population age 65 and over.

A single mutation (R345W) in the EGF-containing fibrillin-like extracellular matrix protein 1 (EFEMP1) gene on chromosome 2 is responsible for the ML phenotype in humans. The EFEMP1 protein, also known as S1-5, FBNL, or fibulin-3, is a 493-amino acid protein in the fibulin family of extracellular matrix proteins. EFEMP1 is a secreted extracellular matrix protein, however, its function remains unknown.

In the normal human retina, EFEMP1 protein localizes outside the apical membrane of the retinal pigment epithelial (RPE) cells, in the region of the photoreceptor inner and outer segments. However, in retinas from ML and AMD patients, EFEMP1 localizes to a region between the RPE and drusen.

Adeno-associated virus (AAV) is the smallest of known human viruses. There is no disease which has been to date associated with AAV. It incorporates into the host cell's genome, but there is no evidence that it can cause malignant transformation. Because of these features it presents an attractive subject for creating vectors for gene therapy.

AAV advantages for gene therapy include: the lack of pathogenicity, the ability to infect non-dividing cells and the ability to stably integrate into the host cell genome at a specific site (designated AAVS1) in the human 19th chromosome. The last feature makes it superior to retroviruses, which present threat of a random insertion and of mutagenesis, which is sometimes followed by development of a cancer. The AAV genome integrates most frequently into the site mentioned, while random incorporations into the genome take place with a negligible frequency. AAVs also present very low immunogenicity, restricted only to generation of neutralizing antibodies, while they induce no cytotoxic response.

SUMMARY OF THE INVENTION

This invention provides, in one embodiment, a method for transducing a cell comprising primary cilia, comprising the step of administering to a cell a recombinant serotype 2 adeno-associated virus (AAV) vector.

In another embodiment, the present invention provides a method of treating or inhibiting a kidney disease comprising a defective gene in a subject, comprising the steps of exposing the renal collecting duct of a subject to a recombinant serotype 2 adeno-associated virus (AAV) vector comprising a transgene corrective for said kidney disease; and delivering said recombinant AAV to a renal tubular epithelial cell.

In another embodiment, the present invention provides a method of preparing a kidney cell for transplantation, comprising the steps of contacting a kidney cell with a recombinant serotype 2 adeno-associated virus (AAV) vector comprising a transgene encoding a trophic protein.

In another embodiment, the present invention provides a method of preparing a kidney of a subject for transplantation, comprising the steps of exposing the renal collecting duct of a subject; and delivering a recombinant serotype 2 adeno-associated virus (AAV) vector comprising a transgene encoding a trophic protein to a renal tubular epithelial cell.

In another embodiment, the present invention provides a method of treating or inhibiting a macular degeneration disease, comprising a mutated fibrillin-like extracellular matrix protein 1 (EFEMP1) gene in a subject comprising the steps of contacting an eye cell with a recombinant serotype 2 adeno-associated virus (AAV) vector comprising a wild-type EFEMP1 transgene.

In another embodiment, the present invention provides a method for transducing a retinal cell, comprising the step of administering to said retinal cell a recombinant serotype 2 adeno-associated virus (AAV) vector.

In another embodiment, the present invention provides a method for transducing a cochlear cell, comprising the step of administering to a cochlear cell a recombinant serotype 2 adeno-associated virus (AAV) vector.

In another embodiment, the present invention provides a method for transducing a kidney cell, comprising the step of: administering to a kidney cell a recombinant serotype 2 adeno-associated virus (AAV) vector.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE INVENTION

Figure 1A:
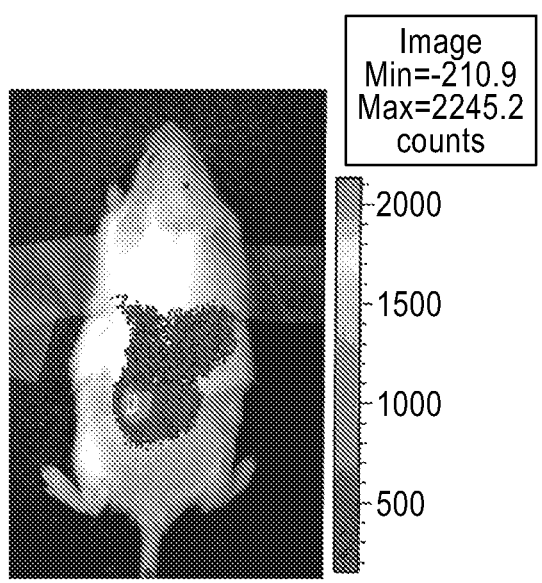
FIG. 1 shows the expression of a reporter gene in the kidney after in vivo administration of novel AAVs carrying CMV.Luciferase (A) or CMV.EGFP (B, C). (A) Non-invasive imaging of luciferase bioluminescence using the Xenogen IVIS system 2 weeks after injection of AAV2/9.CMV. Luciferase to the left ureter. (B) EGFP fluorescence in kidneys dissected from different animals 3 weeks after delivery of the designated AAV to the ureter. Scale bars in (A) and (B) show intensity of transgene expression, with the red color indicating the highest levels. (C) Histological micrographs showing EGFP expression in renal tubular epithelial cells in the medulla after retro-ureteral delivery of AAV.EGFP. Dotted lines on left side of panel delineate the kidney and ureter. Arrows indicate strongly positive EGFP-expressing tubules. Nuclei are stained with DAPI (blue).

In one embodiment, the present invention provides a method for transducing a cell comprising primary cilia, comprising the step of administering to a cell a recombinant serotype 2 adeno-associated virus (AAV) vector. In another embodiment, the present invention provides a method for engineering a cell comprising primary cilia, comprising the step of administering to a cell a recombinant serotype 2 adeno-associated virus (AAV) vector.

In another embodiment, the present invention provides the cell of the invention is a eukaryotic cell. In another embodiment, the present invention provides the cell of the invention is a retinal cell. In another embodiment, the present invention provides the cell of the invention is an otocyst cell. In another embodiment, the present invention provides the cell of the invention is a kidney cell.

In another embodiment, the present invention provides methods for treating, abrogating, or inhibiting a kidney disease. In another embodiment, the present invention provides that a kidney disease is caused by inherited gene defects. In another embodiment, the present invention provides that a kidney disease is caused by damage caused by disease of other organ systems. In another embodiment, the present invention provides that a kidney disease is caused by diabetes. In another embodiment, the present invention provides that a kidney disease is caused by hemolytic uremic syndrome. In another embodiment, the present invention provides that a kidney disease is caused by Lupus nephritis. In another embodiment, the present invention provides that a kidney disease is caused by high blood pressure. In another embodiment, the present invention provides that a kidney disease is caused by an immune disorder. In another embodiment, the present invention provides that a kidney disease is caused by an infection. In another embodiment, the present invention provides that a kidney disease is caused by exposure to toxic chemicals.

Kidney Disease

In another embodiment, the present invention provides a method of treating a kidney disease comprising a defective gene in a subject, comprising the steps of: exposing the renal collecting duct of a subject to a recombinant serotype 2 adeno-associated virus (AAV) vector comprising a transgene corrective for a kidney disease; and delivering the recombinant AAV to a renal tubular epithelial cell. In another embodiment, the present invention provides a method of inhibiting a kidney disease comprising a defective gene in a subject, comprising the steps of: exposing the renal collecting duct of a subject to a recombinant serotype 2 adeno-associated virus (AAV) vector comprising a transgene corrective for a kidney disease; and delivering the recombinant AAV to a renal tubular epithelial cell. In another embodiment, the present invention provides a method of abrogating a kidney disease comprising a defective gene in a subject, comprising the steps of: exposing the renal collecting duct of a subject to a recombinant serotype 2 adeno-associated virus (AAV) vector comprising a transgene corrective for a kidney disease; and delivering the recombinant AAV to a renal tubular epithelial cell. In another embodiment, the present invention provides a method of reversing a kidney disease comprising a defective gene in a subject, comprising the steps of: exposing the renal collecting duct of a subject to a recombinant serotype 2 adeno-associated virus (AAV) vector comprising a transgene corrective for a kidney disease; and delivering the recombinant AAV to a renal tubular epithelial cell.

In another embodiment, the present invention provides a method of treating a Bardet-Biedl syndrome. In another embodiment, the present invention provides a method of treating an Alport syndrome.

In another embodiment, the present invention provides that an inherited kidney disease is caused by mutations in genes expressed by renal tubular epithelial cells. In another embodiment, renal tubular epithelial cells are the cells which line the collecting ducts of the kidney. In another embodiment, mutations that affect renal tubular epithelial cells cause cellular dysfunction. In another embodiment, mutations that affect renal tubular epithelial cells cause disorganization and death of these cells. In another embodiment, mutations that affect renal tubular epithelial cells cause cyst formation.

In another embodiment, kidney diseases caused by mutations in genes expressed by renal tubular epithelial cells are common potentially lethal genetic disorders in humans. In another embodiment, poly cystic kidney disease (PKD) is an example of such diseases. In another embodiment, PKD results in cystic and tubular overgrowth that leads to destruction of the normal kidney architecture and renal failure. In another embodiment, the present invention provides that PKD results from a mutation in pkd1 gene. In another embodiment, the present invention provides that PKD results from a mutation in pkd2 gene. In another embodiment, poly cystic kidney disease (PKD) of the present invention is autosomal dominant PKD (ADPKD).

In another embodiment, the present invention provides methods of treating kidney diseases comprising gene-based delivery of corrective proteins. In another embodiment, the present invention provides methods of treating PKD comprising gene-based delivery of corrective proteins. In another embodiment, the present invention provides methods of treating ADPKD comprising gene-based delivery of corrective proteins. In another embodiment, the present invention provides methods of treating a kidney disease comprising delivery of anti-apoptotic genes. In another embodiment, the present invention provides methods of treating a kidney disease comprising delivery of growth factors genes.

In another embodiment, the present invention provides methods of treatment which comprise correcting a pathologic defect. In another embodiment, the present invention provides methods of treatment which comprise reversing a kidney pathology. In another embodiment, the present invention provides methods of treating a kidney disease or pathology comprise correcting a pathologic defect originating from a mutated pkd1 gene or pkd2 gene. In another embodiment, the present invention provides methods of treating a kidney disease or pathology comprise correcting a pathologic defect characterized by a mutated pkd1 gene or pkd2 gene.

In another embodiment, the present invention provides a transgene comprising pkd1 wild type gene or pkd2 wild type gene for treating a kidney disease or pathology. In another embodiment, the present invention provides a transgene comprising pkd1 wild type gene or pkd2 wild type gene for ameliorating a kidney disease or pathology. In another embodiment, the present invention provides a transgene comprising pkd1 wild type gene or pkd2 wild type gene for inhibiting a kidney disease or pathology. In another embodiment, the present invention provides a transgene comprising pkd1 wild type gene or pkd2 wild type gene for reversing a kidney disease or pathology.

In another embodiment, the present invention provides methods of treating a kidney disease or pathology comprise correcting a pathologic defect originating from a mutated intraflagellar transport 88 (uft88) gene. In another embodiment, the present invention provides methods of treating a kidney disease or pathology comprise correcting a pathologic defect characterized by a mutated uft88 gene.

In another embodiment, the present invention provides a transgene comprising uft88 wild type gene for treating a kidney disease or pathology. In another embodiment, the present invention provides a transgene comprising uft88 wild type gene for ameliorating a kidney disease or pathology. In another embodiment, the present invention provides a transgene comprising uft88 wild type gene for inhibiting a kidney disease or pathology. In another embodiment, the present invention provides a transgene comprising uft88 wild type gene for reversing a kidney disease or pathology.

In another embodiment, the present invention provides a method of preparing a kidney cell comprising primary cilia for transplantation, comprising the steps of: contacting a cell with a recombinant serotype 2 adeno-associated virus (AAV) vector comprising a transgene encoding a trophic protein. In another embodiment, the present invention provides a method of preparing a kidney cell for transplantation, comprising the steps of: contacting a cell with a recombinant serotype 2 adeno-associated virus (AAV) vector comprising a transgene encoding a trophic protein.

In another embodiment, the trophic transgene provides trophic support for kidneys prior to transplant. In another embodiment, the trophic transgene provides trophic support for kidneys prior to transplant in order to prolong storage while identifying recipient patients or in transporting the tissue to the transplant site. In another embodiment, the trophic transgene provides trophic support of kidney cells prior to transplant in order to prolong storage.

In another embodiment, the present invention provides a method of preparing a kidney of a subject for transplantation, comprising the steps of: exposing the renal collecting duct of said subject; and delivering a recombinant serotype 2 adeno-associated virus (AAV) vector comprising a transgene encoding a trophic protein to a renal tubular epithelial cell. In another embodiment, the present invention provides a method of preparing a kidney of a human subject for transplantation, comprising the steps of: exposing the renal collecting duct of said subject; and delivering a recombinant serotype 2 adeno-associated virus (AAV) vector comprising a transgene encoding a trophic protein to a renal tubular epithelial cell. In another embodiment, the present invention provides a method of preparing a kidney of a subject for transplantation, comprising retrograde ureteral delivery of a recombinant serotype 2 adeno-associated virus (AAV) vector comprising a transgene encoding a trophic protein to a renal tubular epithelial cell.

In another embodiment, the present invention provides a method for transducing a kidney cell, comprising the step of: administering to a kidney cell a recombinant serotype 2 adeno-associated virus (AAV) vector. In another embodiment, the present invention provides a method for engineering a kidney cell, comprising the step of: administering to a kidney cell a recombinant serotype 2 adeno-associated virus (AAV) vector. In another embodiment, kidney cell is a ciliated kidney cell.

In another embodiment, the present invention provides methods that correct the cellular defect and reverse or halt progression of the kidney disease. In another embodiment, the present invention provides methods for treating a kidney disease comprising delivering corrective genes through a single endoscopic application to renal tubular epithelial cells. In another embodiment, the methods of the present invention provide that delivery is achieved through a non-invasive approach.

In another embodiment, the methods of the present invention provide that delivery is achieved through retrograde ureteral delivery. In another embodiment, the methods of the present invention provide that delivery is achieved through direct injection into the parenchyma.

In another embodiment, the term "corrective genes" comprises wild-type gene that corrects the corresponding mutated gene. In another embodiment, the term "corrective genes" comprises growth factors that treat or reverse a pathology characterized by being responsive to growth factors as known to one of skill in the art. In another embodiment, the term "corrective genes" comprises anti-apoptotic genes that treat or reverse a pathology characterized by elevated, undesired apoptotic rate as known to one of skill in the art. In another embodiment, the term "corrective genes" comprises pro-apoptotic and/or anti-cancer genes that treat or reverse a pathology such as but not limited to cancer or uncontrolled tissue growth as known to one of skill in the art. In another embodiment, the term "corrective genes" comprises trophic genes encoding trophic proteins such as growth factors or immune system modulators which provide trophic support and are administered for example to a kidney cell or a kidney prior to being transplanted.

In another embodiment, the methods of the present invention provide the use of a recombinant adeno-associated virus (AAV) for carrying the corrective gene. In another embodiment, the methods of the present invention provide that an AAV carrying the corrective gene can treat a kidney disease of the invention. In another embodiment, the methods of the present invention provide that an AAV carrying the corrective gene is applied to the kidney through a retrograde access. In another embodiment, the methods of the present invention provide that an AAV carrying the corrective gene is applied to the kidney through the renal collecting duct system. In another embodiment, the methods of the present invention provide that an AAV delivered in this manner delivers the corrective gene(s) to renal tubular epithelial cells efficiently and in a stable fashion. In another embodiment, the methods of the present invention provide that an AAV delivered in this manner corrects the pathologic defect in the kidney. In another embodiment, the methods of the present invention provide that an AAV delivered in this manner reverses the kidney pathology. In another embodiment, the methods of the present invention provide that an AAV delivered in this manner minimizes immunologic response to the foreign AAV capsid antigens. In another embodiment, the methods of the present invention provide that distal renal tubular epithelial cells are post-mitotic and thus stable expression of the corrective protein(s) is ensured.

In another embodiment, the present invention provides that the AAV vector comprises a reporter gene. In another embodiment, the reporter gene is a fluorescent protein. In another embodiment, the reporter gene comprises green fluorescent proteins such as but not limited to: GFP, Emerald, Azami Green, or ZsGreen1. In another embodiment, the reporter gene comprises blue fluorescent proteins such as but not limited to: EBFP or Sapphire. In another embodiment, the reporter gene comprises cyan fluorescent proteins such as but not limited to: Cerulean, ECFP, AmCyan1 or Midoriishi-Cyan. In another embodiment, the reporter gene comprises yellow fluorescent proteins such as but not limited to: ZsYellow1, PhiYFP, Citrine, or Venus. In another embodiment, the reporter gene comprises orange fluorescent proteins such as but not limited to: Kusabira-Orange or mOrange. In another embodiment, the reporter gene comprises red fluorescent proteins such as but not limited to: DsRed, HcRed, mPlum, mRaspberry, mTomato, mStrawberry. In another embodiment, the reporter gene comprises a green-to-red fluorescent Dendra.

In another embodiment, the identifiable gene product serves as a distinguishable marker between cells transduced by the AAV vector of the present invention and cells that were not transduced by the AAV vector of the present invention. In another embodiment, the present invention comprises a luminescent reporter gene. In another embodiment, the luminescent reporter gene of the present invention comprises is luciferase (FIG. 1).

Figure 1C:
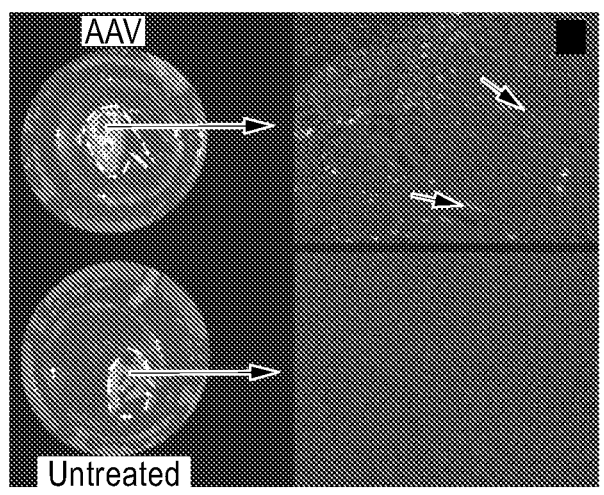
Figure 1B:
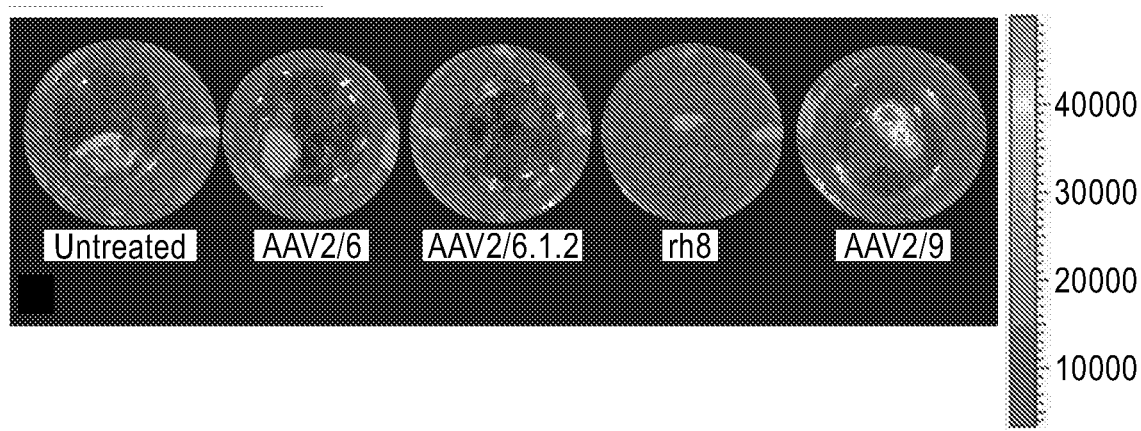

In another embodiment, the present invention provides that kidneys are injected via a retrograde approach with AAVs carrying luciferase (FIG. 1 A). In another embodiment, the present invention provides that kidneys are injected via a retrograde approach with AAVs carrying enhanced green fluorescent protein (EGFP) (FIG. 1B-C).

In another embodiment, the present invention provides utilization of gene therapy to cure or ameliorate autosomal Dominant Polycystic Kidney Disease (ADPKD) in an animal model. In another embodiment, the present invention provides utilization of gene therapy to cure or ameliorate autosomal Dominant Polycystic Kidney Disease (ADPKD) in a mouse model. In another embodiment, the present invention provides utilization of gene therapy to cure or ameliorate autosomal Dominant Polycystic Kidney Disease (ADPKD) in humans.

In another embodiment, the present invention provides that primary cilia are highly conserved throughout evolution. In another embodiment, the present invention provides that the primary cilium is an organelle found on renal tubular epithelial cells that appears to act as a mechanosensor of urinary flow, and utilizes calcium as an intracellular second messenger.

In another embodiment, the present invention provides that mutations in the pkd1 or pkd2 genes, which encode the integral membrane proteins polycystin-1 and polycystin-2, lead to ADPKD. In another embodiment, the present invention provides that polycystins 1 and 2 interact and polycystin-2 is a calcium channel. In another embodiment, the present invention provides that a mouse model of ADPKD, involving loss of polycystin-2, exists: $pkd2^{WS25/WS183}$. In another embodiment, the present invention provides that cells deficient in polycystin-2 contain normal appearing, but non-functional, primary cilia, as the increase in intracellular calcium following mechanical stimulation of cilia no longer occurs.

In another embodiment, the present invention provides defects in function of renal tubular cell primary cilia cause ADPKD. In another embodiment, the present invention provides that gene therapy using AAV can rescue these defects. In another embodiment, the present invention provides that AAV vectors are delivered by a trans-ureteral delivery route. In another embodiment, the present invention provides that trans-ureteral delivery route minimizes the potential of immunologic toxicity. In another embodiment, the present invention provides rescue of cystic phenotype in $Pkd2^{WS2/WS183}$ mice, using retrograde injection of AAV encoding wild-type polycystin-2. In another embodiment, the present invention provides that functional rescue of renal primary cilia comprise co-localization of polycystin-2 and calcium influx in response to flow in collecting duct cells.

In another embodiment, the present invention provides that pkd2 encoding polycystin-2, weighs 110 kDa and contains 968 amino acids. In another embodiment, the present invention provides that pkd2 use in gene therapy is feasible using the present methods. In another embodiment, the present invention provides that pkd1 is used in gene therapy methods of the present invention. In another embodiment, the present invention provides that pkd2 gene therapy reduces the cystic burden. In another embodiment, the present invention provides the use of AAV in retrograde injection via endoscopic techniques.

The AAV

In another embodiment, the methods of the present invention provide gene therapy. In another embodiment, the methods of the present invention provide the introduction of a functional gene into a target ciliated cell to restore proper protein production that is absent or deficient due to a genetic disorder. In another embodiment, the methods of the present invention provide the introduction of a functional gene into a target ciliated cell to induce protein production that is necessary for applications such as but not limited to kidney cell transplantation. In another embodiment, the methods of the present invention provide the introduction of a functional gene into a target ciliated cell to induce protein production that is necessary for applications such as but not limited to kidney transplantation.

In another embodiment, the methods of the present invention provide viral delivery systems that are based on viruses that have the ability to deliver genetic information into the host ciliated cell. In another embodiment, the methods of the present invention provide the generation of a replication-defective viral vector. In another embodiment, the methods of the present invention provide that the coding regions of the virus are replaced by the genetic information of a therapeutic gene. In another embodiment, the methods of the present invention provide the coding regions of the virus are replaced by the genetic information of a therapeutic gene leaving the cis-acting sequences intact. In another embodiment, the methods of the present invention provide that the viral vector is introduced into producer cells providing the structural viral proteins in trans, production of nonreplicating virus particles containing the genetic information of a therapeutic gene is established. In another embodiment, the methods of the present invention provide the ability to generate replication-defective viral vectors for virus-based gene delivery vehicles.

In another embodiment, the methods of the present invention provide integrating vectors. In another embodiment, the methods of the present invention provide nonintegrating vectors. In another embodiment, the methods of the present invention provide vectors based on adeno-associated virus and retroviruses (including lentivirus and foamy virus) that have the ability to integrate their viral genome into the chromosomal DNA of the host cell. In another embodiment, the methods of the present invention provide a lifelong gene expression.

In another embodiment, the methods of the present invention provide a parvoviridae vector. In another embodiment, the methods of the present invention provide a dependoviruse vector. In another embodiment, the methods of the present invention provide an AAV vector. In another embodiment, the methods of the present invention provide a nonpathogenic and by nonreplicating vector.

In another embodiment, the methods of the present invention provide an AAV virion that is in the form of a nonenveloped particle (20-25 nm) that carry a linear single-stranded DNA (ssDNA) genome. In another embodiment, the methods of the present invention provide an AAV virion that is in the form of an enveloped particle that carry a linear single-stranded DNA (ssDNA) genome.

In another embodiment, the methods of the present invention provide an AAV vector comprise the ITRs. In another embodiment, the methods of the present invention provide an AAV vector comprise the ITRs and 45 adjacent bp that display cis-acting functions essential for virus production and integration. In another embodiment, the methods of the present invention provide that AAV vector comprises a promoter and a transgene flanked by ITRs. In another embodiment, the methods of the present invention provide that an AAV vector comprising the ITRs and 45 adjacent bp that display cis-acting functions prevents the formation of replication competent AAV during vector production. In another embodiment, the methods of the present invention provide that Rep and cap proteins are produced in trans in the packaging cells, whereas coinfection with Ad provides the necessary Ad proteins for initiation of vector replication.

In another embodiment, the methods of the present invention provide the production systems that are free of replicating Ad. In another embodiment, the methods of the present invention provide that Ad proteins E2A, VA, and E4 are expressed from a second helper construct in the host cells, which provides E1A and E1B gene products. In another embodiment, the methods of the present invention provide that the reduction of rep production from the helper construct prevents the cytotoxicity in the packaging cells, which subsequently improves vector production.

In another embodiment, the methods of the present invention provide an AAV serotype 2 (AAV-2) vectors. In another embodiment, the methods of the present invention provide that AAV-2 is efficient in transducing the ciliated cells of the invention. In another embodiment, the methods of the present invention provide that AAV-2 is efficient in engineering the ciliated cells of the invention. In another embodiment, the methods of the present invention provide AAV-1 vectors. In another embodiment, the methods of the present invention provide AAV-3 vectors. In another embodiment, the methods of the present invention provide AAV-4 vectors. In another embodiment, the methods of the present invention provide AAV-5 vectors. In another embodiment, the methods of the present invention provide that AAV-5 is efficient in transducing airway epithelia cells. In another embodiment, the methods of the present invention provide that AAV-5 is efficient in engineering airway epithelia cells. In another embodiment, the methods of the present invention provide that the use of different AAV serotypes may allow targeting of the vector for tissue-specific transduction. In another embodiment, the methods of the present invention provide altering the tropism of AAV vectors by chemical cross-linking of bispecific antibodies to the viral capsid and by the insertion of receptor specific epitopes in the cap proteins.

In another embodiment, the methods of the present invention provide that ssDNA genome of the vectors is converted into a dsDNA. In another embodiment, the methods of the present invention provide that transduction occurs in the absence of a helper virus and rep proteins. In another embodiment, the methods of the present invention provide that AAV relies solely on cellular conditions supporting this event.

In another embodiment, the methods of the present invention provide that AAV vectors of the invention are endemic to human populations and are non-toxic. In another embodiment, the methods of the present invention provide that AAV vectors of the invention exhibit no known clinical sequels and minimal immunogenicity. In another embodiment, the methods of the present invention provide that AAV vectors of the invention comprise endosomal entry. In another embodiment, the methods of the present invention provide that AAV capsid is composed of 60 subunits, comprising 3 closely related proteins (VP1, 90 kDa; VP2, 72 kDa; VP3, 60 kDa) in a weakly bonded network. In another embodiment, the methods of the present invention provide that AAV vectors of the invention are engineerable by means of molecular biology, making it possible to optimize these vectors for cell specific delivery of genetic material, for minimizing immunogenicity, for particle lifetime, and for efficient degradation.

In another embodiment, the methods of the present invention provide that AAV vector transduction occurs in the absence of cell cycle. In another embodiment, the methods of the present invention provide that transduction efficiency is markedly improved in cells in S-phase. In another embodiment, the methods of the present invention provide transduction of terminally differentiated postmitotic cells.

In another embodiment, the methods of the present invention provide that the AAV vector dsDNA genomes of the invention persist in transduced cells for long periods of time and are able to form concatamers by head to tail recombination of the ITRs. In another embodiment, the methods of the present invention provide that integration of single and concatameric genomes occurs randomly in the host ciliated cell genome. In another embodiment, the methods of the present invention provide that the transgene is predominantly expressed from episomal forms.

In another embodiment, the methods of the present invention makes use of the unique ability of AAV to form concatamers by head to tail recombination of the ITRs, increasing delivery size up to 10 kb. In another embodiment, the methods of the present invention provide that promoter and transgene sequences are split over two AAV vectors. In another embodiment, the methods of the present invention provide that the two vectors are used to transduce cells, resulting in expression of a functional gene is obtained after head to tail recombination of the two viral genomes.

In another embodiment, the methods of the present invention provide that the AAV vectors of the invention comprise cap proteins from different serotypes that overcome the problems of neutralizing antibodies.

In another embodiment, the methods of the present invention provide a gutless Ad vector, which is deprived of nearly all viral sequences, prevents elimination of transduced cells by the immune system, thus allowing long term transgene expression. In another embodiment, the methods of the present invention provide an Ad/AAV or Ad/retrovirus hybrid vectors. In another embodiment, the methods of the present invention provide that these vectors are devoid of all viral genes, and the transgene sequence is flanked by AAV ITRs or retroviral LTRs. In another embodiment, the methods of the present invention provide that these cis-acting elements from unrelated viruses allow integration of the transgene by host cell enzymes in the absence of viral proteins (AAV rep and retroviral integrase) supporting these events.

In another embodiment, the methods of the present invention provide that gutless Ad vectors markedly reduce inflammatory responses and cellular infiltration.

In another embodiment, the present invention provides that the AAV used by the methods of the present invention is an AAV serotype 1. In another embodiment, the present invention provides that the AAV used by the methods of the present invention is an AAV serotype 2. In another embodiment, the present invention provides that the AAV used by the methods of the present invention is an AAV serotype 3. In another embodiment, the present invention provides that the AAV used by the methods of the present invention is an AAV serotype 4. In another embodiment, the present invention provides that the AAV used by the methods of the present invention is an AAV serotype 5. In another embodiment, the present invention provides that the AAV of the present invention comprises AAV serotype 2 inverted terminal repeats (ITRs) and packaged into capsids from AAV serotype 1, 2, 5, 8, or 9. In another embodiment, the present invention provides that the AAV of the present invention comprises AAV serotype 1 ITRs and packaged into capsids from AAV serotype 1, 2, 5, 8, or 9.

In another embodiment, the present invention provides that the AAV used by the methods of the present invention is a hybrid AAV vector. In another embodiment, the methods of the present invention provide that an AAV vector is packaged in a capsid from an AAV of other serotypes.

In another embodiment, the present invention provides that a hybrid AAV vector of the present invention comprises ITRs belonging to a first serotype and a capsid belonging to a second serotype. In another embodiment, the present invention provides that the AAV of the present invention comprises AAV serotype 2 ITRs and packaged into capsids from AAV serotype 1. In another embodiment, the present invention provides that the AAV of the present invention comprises AAV serotype 2 ITRs and packaged into capsids from AAV serotype 2. In another embodiment, the present invention provides that the AAV of the present invention comprises AAV serotype 2 ITRs and packaged into capsids from AAV serotype 5. In another embodiment, the present invention provides that the AAV of the present invention comprises AAV serotype 2 ITRs and packaged into capsids from AAV serotype 8. In another embodiment, the present invention provides that the AAV of the present invention comprises AAV serotype 2 ITRs and packaged into capsids from AAV serotype 9.

In another embodiment, the methods of the present invention provide that an AAV vector comprises a transgene bounded by inverted terminal repeats (ITRs). In another embodiment, the methods of the present invention provide that the ITRs are of serotype 2 AAV.

In another embodiment, the present invention provides that the AAV of the present invention comprises AAV serotype 1 ITRs and packaged into capsids from AAV serotype 1. In another embodiment, the present invention provides that the AAV of the present invention comprises AAV serotype 1 ITRs and packaged into capsids from AAV serotype 2. In another embodiment, the present invention provides that the AAV of the present invention comprises AAV serotype 1 ITRs and packaged into capsids from AAV serotype 5. In another embodiment, the present invention provides that the AAV of the present invention comprises AAV serotype 1 ITRs and packaged into capsids from AAV serotype 8. In another embodiment, the present invention provides that the AAV of the present invention comprises AAV serotype 1 ITRs and packaged into capsids from AAV serotype 9.

In another embodiment, the present invention provides that ciliated cells are targeted by the methods of the present invention. In another embodiment, the present invention provides that ciliated cells are transduced by the methods of the present invention. In another embodiment, the present invention provides that ciliated cells are engineered by the methods of the present invention. In another embodiment, the present invention provides that ciliated cells are treated by the methods of the present invention. In another embodiment, the present invention provides that ciliated cells are targeted, treated, transduced, or engineered by the methods of the present invention which comprise the use of an engineered AAV. In another embodiment, the present invention provides that ciliated cells are targeted, treated, transduced, or engineered by the methods of the present invention which comprise the use of a recombinant AAV. In another embodiment, the present invention provides that ciliated cells are targeted, treated, transduced, or engineered by the methods of the present invention which comprise the use of a hybrid AAV.

In another embodiment, AAV vectors of the present invention are delivered to cultured cells. In another embodiment, AAV vectors of the present invention are delivered to cultured collecting duct cells. In another embodiment, AAV vectors of the present invention are delivered to cultured iMCD3 cells. In another embodiment, these cells are cultured as confluent epithelial monolayers on Transwell filters. In another embodiment, infections is performed using $5\times10^9$ genome copies per well of cells. In another embodiment, infections is performed using $5\times10^7$-$5\times10^9$ genome copies per well of cells. In another embodiment, infections is performed using $5\times10^5$-$5\times10^9$ genome copies per well of cells. In another embodiment, infections is performed using $5\times10^3$-$5\times10^5$ genome copies per well of cells. In another embodiment, infections is performed using $5\times10^9$-$5\times10^{11}$ genome copies per well of cells. In another embodiment, infections is performed using $5\times10^{11}$-$5\times10^{13}$ genome copies per well of cells.

In another embodiment, the present invention provides that a constitutive promoter is used to drive the transgene expression. In another embodiment, the present invention provides that the transgene comprise EGFP-luciferase fusion cDNA. In another embodiment, the present invention provides that quantitative data is obtained by measuring luciferase bioluminescence using the Xenogen Imaging system. In another embodiment, the present invention provides that qualitative data is evaluated via fluorescence microscopy.

In another embodiment, the present invention provides transduction patterns and transgene expression after subretinal, otocyst, and retrograde ureteral delivery of transgenes through hybrid AAVs. In another embodiment, the present invention provides unilateral subretinal, intra-otocyst, and retrograde ureteral injections of hybrid AAVs. In another embodiment, the present invention provides that the transgene cassette comprises of a CMV-promoted EGFP and/or a luciferase transgene. In another embodiment, the present invention provides that the transgene cassette comprises of a CMV-promoted corrective transgene.

In another embodiment, the present invention provides that cellular specificity of expression is evaluated histologically. In another embodiment, the present invention provides that onset of transgene expression is between 1-10 days. In another embodiment, the present invention provides that onset of transgene expression is between 3-7 days. In another embodiment, the present invention provides that onset of transgene expression is between 6-10 days.

In another embodiment, the present invention provides that onset of transgene expression is between 10-30 days. In another embodiment, the present invention provides that onset of transgene expression is between 10-20 days. In another embodiment, the present invention provides that onset of transgene expression is between 15-25 days. In another embodiment, the present invention provides that onset of transgene expression is between 20-30 days.

In another embodiment, the present invention provides that onset of transgene expression is between 30-180 days. In another embodiment, the present invention provides that onset of transgene expression is between 30-70 days. In another embodiment, the present invention provides that onset of transgene expression is between 50-100 days. In another embodiment, the present invention provides that onset of transgene expression is between 80-120 days. In another embodiment, the present invention provides that onset of transgene expression is between 100-150 days. In another embodiment, the present invention provides that onset of transgene expression is between 140-180 days.

In another embodiment, the present invention provides that onset of transgene expression is between 180-1000 days. In another embodiment, the present invention provides that onset of transgene expression is between 180-500 days. In another embodiment, the present invention provides that onset of transgene expression is between 180-300 days. In another embodiment, the present invention provides that onset of transgene expression is between 250-400 days. In another embodiment, the present invention provides that onset of transgene expression is between 300-500 days. In another embodiment, the present invention provides that onset of transgene expression is between 450-550 days. In another embodiment, the present invention provides that onset of transgene expression is between 500-700 days. In another embodiment, the present invention provides that onset of transgene expression is between 600-800 days. In another embodiment, the present invention provides that onset of transgene expression is between 700-900 days. In another embodiment, the present invention provides that onset of transgene expression is between 750-1000 days.

In another embodiment, the present invention provides that onset of transgene expression is between 1000-20000 days. In another embodiment, the present invention provides that onset of transgene expression is between 1000-2000 days. In another embodiment, the present invention provides that onset of transgene expression is between 1000-5000 days. In another embodiment, the present invention provides that onset of transgene expression is between 2000-4000 days. In another embodiment, the present invention provides that onset of transgene expression is between 4000-7000 days. In another embodiment, the present invention provides that onset of transgene expression is between 5000-8000 days. In another embodiment, the present invention provides that onset of transgene expression is between 6000-10000 days. In another embodiment, the present invention provides that onset of transgene expression is between 8000-12000 days. In another embodiment, the present invention provides that onset of transgene expression is between 10000-15000 days. In another embodiment, the present invention provides that onset of transgene expression is between 12000-16000 days. In another embodiment, the present invention provides that onset of transgene expression is between 140000-18000 days. In another embodiment, the present invention provides that onset of transgene expression is between 16000-20000 days.

In another embodiment, the present invention provides that modifications of AAV capsids allow efficient transduction of specific subsets of cells with primary cilia. In another embodiment, the present invention provides that modifications of AAV capsids allow efficient transduction of photoreceptors cells. In another embodiment, the present invention provides that modifications of AAV capsids allow efficient transduction of cochlear hair cells. In another embodiment, the present invention provides that modifications of AAV capsids allow efficient transduction of renal tubular epithelial cells.

Ciliated Cells

In another embodiment, ciliated cells of the present invention comprise primary cilia. In another embodiment, cilia of the present invention function as a mechano-sensor. In another embodiment, cilia of the present invention function as a chemo-sensor. In another embodiment, cilia of the present invention functions both as a mechano-sensor and a chemo-sensor. In another embodiment, cilia of the present invention function both as a mechano-sensor and a chemo-sensor in renal tubular epithelia.

In another embodiment, cilia of the present invention are critically involved in the determination of left-right siddness during development. In another embodiment, cilia of the present invention are a key factor in the development of polycystic kidney disease, as well as a number of other abnormalities.

In another embodiment, the primary cilium is a solitary cellular structure. In another embodiment, the primary cilium of the present invention has a so-called 9+0 axoneme, which refers to its nine peripherally located microtubule pairs and the absence of the central microtubule pair seen in motile cilia or 9+2 cilia.

In another embodiment, the present invention comprises a blastocyst comprising a nodal cilium in which does have radial spokes and dynein arms but lacks a central pair of microtubules. In another embodiment, nodal flow is disturbed by mutations in either the genes coding for the motor molecules or those coding for the proteins necessary for normal intraflagellar transport (IFT). In another embodiment, the methods of the present invention correct mutations that result in defective dynein, for example, the inv gene that encodes for left-right dynein, also result in nonmotile nodal cilia and situs inversus. In another embodiment, the methods of the present invention reverse mutations that result in defective dynein, for example, the inv gene that encodes for left-right dynein, also result in nonmotile nodal cilia and situs inversus. In another embodiment, the methods of the present invention insert a wild type gene copy in place of a mutated gene copy that result in defective dynein, for example, the inv gene that encodes for left-right dynein.

In another embodiment, the cells transduced by the methods of the present invention comprise motile nodal cilia. In another embodiment, the cells transduced by the methods of the present invention comprise nonmotile primary cilia.

In another embodiment, the cells of the present invention comprise cilia ranging from 1 to 15 μm long. In another embodiment, the cells of the present invention comprise cilia ranging from 2 to 10 μm long. In another embodiment, the cells of the present invention comprise cilia ranging from 10 to 15 μm long. In another embodiment, the cells of the present invention comprise cilia ranging from 12 to 15 μm long. In another embodiment, the cells of the present invention comprise cilia ranging from 3 to 7 μm long. In another embodiment, the cells of the present invention comprise cilia ranging from 2 to 5 μm long. In another embodiment, the cells of the present invention comprise cilia ranging from 5 to 10 μm long. In another embodiment, the cells of the present invention comprise cilia ranging from 5 to 8 μm long.

In another embodiment, the cells of the present invention are able to sense flow through the cilia. In another embodiment, the cells of the present invention increase their intracellular Ca2+ due to flow response. In another embodiment, kidney cells of the present invention are able to sense flow through the cilia. In another embodiment, kidney cells of the present invention increase their intracellular Ca2+ due to flow response.

In another embodiment, primary cilia are present in secretory cells. In another embodiment, primary cilia are present in alpha, beta, and gamma cells of the endocrine pancreas.

In another embodiment, the methods of the present invention are preformed on a cell. In another embodiment, the cell of the present invention is a eukaryotic cell. In another embodiment, the cell of the present invention is an epidermal keratinocyte. In another embodiment, the cell of the present invention is an epidermal basal cell. In another embodiment, the cell of the present invention is a keratinocyte of fingernails or toenails. In another embodiment, the cell of the present invention is a nail bed basal cell. In another embodiment, the cell of the present invention is a stem cell. In another embodiment, the cell of the present invention is a medullary hair shaft cell. In another embodiment, the cell of the present invention is a cortical hair shaft cell. In another embodiment, the cell of the present invention is a cuticular hair shaft cell. In another embodiment, the cell of the present invention is a cuticular hair root sheath cell. In another embodiment, the cell of the present invention is a hair root sheath cell of Huxley's layer. In another embodiment, the cell of the present invention is a hair root sheath cell of Henle's layer. In another embodiment, the cell of the present invention is an external hair root sheath cell. In another embodiment, the cell of the present invention is a hair matrix cell. In another embodiment, the cell of the present invention is a prokaryotic cell.

In another embodiment, the cell of the present invention is a wet stratified barrier epithelial cell. In another embodiment, the cell of the present invention is a surface epithelial cell of stratified squamous epithelium of the cornea. In another embodiment, the cell of the present invention is a surface epithelial cell of stratified squamous epithelium of the tongue. In another embodiment, the cell of the present invention is a surface epithelial cell of stratified squamous epithelium of the oral cavity. In another embodiment, the cell of the present invention is a surface epithelial cell of stratified squamous epithelium of the esophagus. In another embodiment, the cell of the present invention is a surface epithelial cell of stratified squamous epithelium of the anal canal. In another embodiment, the cell of the present invention is a surface epithelial cell of stratified squamous epithelium of the distal urethra. In another embodiment, the cell of the present invention is a surface epithelial cell of stratified squamous epithelium of the vagina.

In another embodiment, the cell of the present invention is a basal cell of epithelia of the cornea. In another embodiment, the cell of the present invention is a basal cell of epithelia of the tongue. In another embodiment, the cell of the present invention is a basal cell of epithelia of the oral cavity. In another embodiment, the cell of the present invention is a basal cell of epithelia of the esophagus. In another embodiment, the cell of the present invention is a basal cell of epithelia of the anal canal. In another embodiment, the cell of the present invention is a basal cell of epithelia of the distal urethra. In another embodiment, the cell of the present invention is a basal cell of epithelia of the vagina.

In another embodiment, the cell of the present invention is a urinary epithelium cell. In another embodiment, the cell of the present invention is an exocrine secretory epithelial cell. In another embodiment, the cell of the present invention is a salivary gland mucous cell. In another embodiment, the cell of the present invention is a salivary gland serous cell. In another embodiment, the cell of the present invention is a Von Ebner's gland cell. In another embodiment, the cell of the present invention is a mammary gland cell. In another embodiment, the cell of the present invention is a lacrimal gland cell. In another embodiment, the cell of the present invention is a ceruminous gland cell. In another embodiment, the cell of the present invention is an eccrine sweat gland dark cell. In another embodiment, the cell of the present invention is an eccrine sweat gland clear cell. In another embodiment, the cell of the present invention is an apocrine sweat gland cell. In another embodiment, the cell of the present invention is a gland of moll cell. In another embodiment, the cell of the present invention is a sebaceous gland cell. In another embodiment, the cell of the present invention is a Bowman's gland cell. In another embodiment, the cell of the present invention is a Brunner's gland cell. In another embodiment, the cell of the present invention is a seminal vesicle cell. In another embodiment, the cell of the present invention is a prostate gland cell. In another embodiment, the cell of the present invention is a bulbourethral gland cell. In another embodiment, the cell of the present invention is a Bartholin's gland cell. In another embodiment, the cell of the present invention is a gland of Littre cell. In another embodiment, the cell of the present invention is a uterus endometrium cell. In another embodiment, the cell of the present invention is a goblet cell. In another embodiment, the cell of the present invention is a stomach lining mucous cell.

In another embodiment, the cell of the present invention is a gastric gland cell. In another embodiment, the cell of the present invention is a gastric gland zymogenic cell. In another embodiment, the cell of the present invention is a gastric gland oxyntic cell. In another embodiment, the cell of the present invention is a pancreatic cell. In another embodiment, the cell of the present invention is a pancreatic acinar cell. In another embodiment, the cell of the present invention is a paneth cell. In another embodiment, the cell of the present invention is a pneumocyte. In another embodiment, the cell of the present invention is a Clara cell of lung.

In another embodiment, the cell of the present invention is a hormone secreting cell. In another embodiment, the cell of the present invention is an anterior pituitary cell. In another embodiment, the cell of the present invention is a somatotrope. In another embodiment, the cell of the present invention is a lactotrope. In another embodiment, the cell of the present invention is a thyrotrope. In another embodiment, the cell of the present invention is a gonadotrope. In another embodiment, the cell of the present invention is a corticotrope. In another embodiment, the cell of the present invention is an intermediate pituitary cell. In another embodiment, the cell of the present invention is a magnocellular neurosecretory cell. In another embodiment, the cell of the present invention is an oxytocin secreting cell. In another embodiment, the cell of the present invention is a serotonin secreting cell. In another embodiment, the cell of the present invention is an endorphin secreting cell. In another embodiment, the cell of the present invention is a somatostatin secreting cell. In another embodiment, the cell of the present invention is a gastrin secreting cell. In another embodiment, the cell of the present invention is a secretin secreting cell. In another embodiment, the cell of the present invention is a cholecystokinin secreting cell. In another embodiment, the cell of the present invention is an insulin secreting cell. In another embodiment, the cell of the present invention is a glucagon secreting cell. In another embodiment, the cell of the present invention is a bombesin secreting cell. In another embodiment, the cell of the present invention is a thyroid gland cell. In another embodiment, the cell of the present invention is a thyroid epithelial cell. In another embodiment, the cell of the present invention is a parafollicular cell. In another embodiment, the cell of the present invention is a parathyroid gland cell. In another embodiment, the cell of the present invention is a parathyroid chief cell. In another embodiment, the cell of the present invention is an oxyphil cell.

In another embodiment, the cell of the present invention is an adrenal gland cell. In another embodiment, the cell of the present invention is a chromaffin cell. In another embodiment, the cell of the present invention is a steroid hormones secreting cell. In another embodiment, the cell of the present invention is a Leydig cell. In another embodiment, the cell of the present invention is a theca interna cell. In another embodiment, the cell of the present invention is a corpus luteum cell. In another embodiment, the cell of the present invention is a kidney juxtaglomerular apparatus cell. In another embodiment, the cell of the present invention is a macula densa cell. In another embodiment, the cell of the present invention is a peripolar cell. In another embodiment, the cell of the present invention is a mesangial cell. In another embodiment, the cell of the present invention is an intestinal brush border cell. In another embodiment, the cell of the present invention is an exocrine gland striated duct cell. In another embodiment, the cell of the present invention is a gall bladder epithelial cell. In another embodiment, the cell of the present invention is a kidney proximal tubule brush border cell. In another embodiment, the cell of the present invention is a kidney distal tubule cell. In another embodiment, the cell of the present invention is a ductulus efferens nonciliated cell. In another embodiment, the cell of the present invention is an epididymal principal cell. In another embodiment, the cell of the present invention is an epididymal basal cell.

In another embodiment, the cell of the present invention is a storage cell. In another embodiment, the cell of the present invention is a hepatocyte. In another embodiment, the cell of the present invention is a white fat cell. In another embodiment, the cell of the present invention is a brown fat cell. In another embodiment, the cell of the present invention is a liver lipocyte.

In another embodiment, the cell of the present invention is a barrier function cell. In another embodiment, the cell of the present invention is a type I pneumocyte. In another embodiment, the cell of the present invention is a pancreatic duct cell. In another embodiment, the cell of the present invention is a nonstriated duct cell. In another embodiment, the cell of the present invention is a kidney glomerulus parietal cell. In another embodiment, the cell of the present invention is a kidney glomerulus podocyte. In another embodiment, the cell of the present invention is a loop of Henle thin segment cell. In another embodiment, the cell of the present invention is a kidney collecting duct cell. In another embodiment, the cell of the present invention is a duct cell. In another embodiment, the cell of the present invention is an epithelial cell lining closed internal body cavity. In another embodiment, the cell of the present invention is a blood vessel cell. In another embodiment, the cell of the present invention is a lymphatic vascular endothelial fenestrated cell. In another embodiment, the cell of the present invention is a blood vessel or lymphatic vascular endothelial continuous cell. In another embodiment, the cell of the present invention is a blood vessel or lymphatic vascular endothelial splenic cell. In another embodiment, the cell of the present invention is a synovial cell. In another embodiment, the cell of the present invention is a serosal cell. In another embodiment, the cell of the present invention is a squamous cell. In another embodiment, the cell of the present invention is a columnar cell of endolymphatic sac with microvilli. In another embodiment, the cell of the present invention is a columnar cell of endolymphatic sac without microvilli. In another embodiment, the cell of the present invention is a dark cell. In another embodiment, the cell of the present invention is a vestibular membrane cell. In another embodiment, the cell of the present invention is a stria vascularis basal cell. In another embodiment, the cell of the present invention is a stria vascularis marginal cell. In another embodiment, the cell of the present invention is a cell of Claudius. In another embodiment, the cell of the present invention is a cell of Boettcher. In another embodiment, the cell of the present invention is a choroid plexus cell. In another embodiment, the cell of the present invention is a pia-arachnoid squamous cell. In another embodiment, the cell of the present invention is a pigmented ciliary epithelium cell. In another embodiment, the cell of the present invention is a nonpigmented ciliary epithelium cell. In another embodiment, the cell of the present invention is a corneal endothelial cell. In another embodiment, the cell of the present invention is a ciliated cell with propulsive function. In another embodiment, the cell of the present invention is a respiratory tract ciliated cell. In another embodiment, the cell of the present invention is an oviduct ciliated cell. In another embodiment, the cell of the present invention is a uterine endometrial ciliated cell. In another embodiment, the cell of the present invention is a rete testis ciliated cell. In another embodiment, the cell of the present invention is a ductulus efferens ciliated cell. In another embodiment, the cell of the present invention is a ciliated ependymal cell of central nervous system.

In another embodiment, the cell of the present invention is an extracellular matrix secretion cell. In another embodiment, the cell of the present invention is an ameloblast epithelial cell. In another embodiment, the cell of the present invention is a planum semilunatum epithelial cell. In another embodiment, the cell of the present invention is an organ of Corti interdental epithelial cell. In another embodiment, the cell of the present invention is a fibroblast. In another embodiment, the cell of the present invention is a loose connective tissue fibroblast. In another embodiment, the cell of the present invention is a corneal fibroblast. In another embodiment, the cell of the present invention is a tendon fibroblast. In another embodiment, the cell of the present invention is a bone marrow reticular tissue fibroblast. In another embodiment, the cell of the present invention is a nonepithelial fibroblast. In another embodiment, the cell of the present invention is a pericyte. In another embodiment, the cell of the present invention is a nucleus pulposus cell of intervertebral disc. In another embodiment, the cell of the present invention is a cementoblast. In another embodiment, the cell of the present invention is a cementocyte. In another embodiment, the cell of the present invention is an odontoblast. In another embodiment, the cell of the present invention is an odontocyte.

In another embodiment, the cell of the present invention is a chondrocyte. In another embodiment, the cell of the present invention is a hyaline cartilage chondrocyte. In another embodiment, the cell of the present invention is a fibrocartilage chondrocyte. In another embodiment, the cell of the present invention is an elastic cartilage chondrocyte. In another embodiment, the cell of the present invention is an osteoblast. In another embodiment, the cell of the present invention is an osteocyte. In another embodiment, the cell of the present invention is an osteoprogenitor cell. In another embodiment, the cell of the present invention is a hyalocyte. In another embodiment, the cell of the present invention is a stellate cell. In another embodiment, the cell of the present invention is a contractile cell.

In another embodiment, the cell of the present invention is a muscle cell. In another embodiment, the cell of the present invention is a red skeletal muscle cell. In another embodiment, the cell of the present invention is a white skeletal muscle cell. In another embodiment, the cell of the present invention is an intermediate skeletal muscle cell. In another embodiment, the cell of the present invention is a nuclear bag cell. In another embodiment, the cell of the present invention is a nuclear chain cell. In another embodiment, the cell of the present invention is a satellite cell. In another embodiment, the cell of the present invention is a heart muscle cell. In another embodiment, the cell of the present invention is a nodal heart muscle cell. In another embodiment, the cell of the present invention is a purkinje fiber cell. In another embodiment, the cell of the present invention is a smooth muscle cell. In another embodiment, the cell of the present invention is a myoepithelial cell.

In another embodiment, the cell of the present invention is a blood cell. In another embodiment, the cell of the present invention is an immune system cell. In another embodiment, the cell of the present invention is a red blood cell. In another embodiment, the cell of the present invention is a megakaryocyte. In another embodiment, the cell of the present invention is a monocyte. In another embodiment, the cell of the present invention is macrophage. In another embodiment, the cell of the present invention is an epidermal Langerhans cell. In another embodiment, the cell of the present invention is an osteoclast. In another embodiment, the cell of the present invention is a dendritic cell. In another embodiment, the cell of the present invention is a microglial cell. In another embodiment, the cell of the present invention is a neutrophil. In another embodiment, the cell of the present invention is an eosinophil. In another embodiment, the cell of the present invention is a basophile. In another embodiment, the cell of the present invention is a mast cell.

In another embodiment, the cell of the present invention is a T-Helper cell. In another embodiment, the cell of the present invention is a T-suppressor cell. In another embodiment, the cell of the present invention is a cytotoxic T cell. In another embodiment, the cell of the present invention is a B cell. In another embodiment, the cell of the present invention is a natural killer cell. In another embodiment, the cell of the present invention is a reticulocyte. In another embodiment, the cell of the present invention is a stem cell. In another embodiment, the cell of the present invention is a committed progenitor for the blood and immune system.

In another embodiment, the cell of the present invention is a sensory transducer cell. In another embodiment, the cell of the present invention is an auditory inner hair cell of organ of Corti. In another embodiment, the cell of the present invention is an auditory outer hair cell of organ of Corti. In another embodiment, the cell of the present invention is a basal olfactory epithelium cell. In another embodiment, the cell of the present invention is a cold-sensitive primary sensory neuron. In another embodiment, the cell of the present invention is a heat-sensitive primary sensory neuron. In another embodiment, the cell of the present invention is a merkel cell. In another embodiment, the cell of the present invention is an olfactory receptor neuron. In another embodiment, the cell of the present invention is a pain-sensitive primary sensory neuron. In another embodiment, the cell of the present invention is a photoreceptor rod cell. In another embodiment, the cell of the present invention is a photoreceptor blue-sensitive cone cell. In another embodiment, the cell of the present invention is a photoreceptor green-sensitive cone cell. In another embodiment, the cell of the present invention is a photoreceptor red-sensitive cone cell. In another embodiment, the cell of the present invention is a proprioceptive primary sensory neuron. In another embodiment, the cell of the present invention is a touch-sensitive primary sensory neuron. In another embodiment, the cell of the present invention is a type I carotid body cell. In another embodiment, the cell of the present invention is a type II carotid body cell. In another embodiment, the cell of the present invention is a type I hair cell of vestibular apparatus. In another embodiment, the cell of the present invention is a type II hair cell of vestibular apparatus. In another embodiment, the cell of the present invention is a type I taste bud cell. In another embodiment, the cell of the present invention is an autonomic neuron cell. In another embodiment, the cell of the present invention is a cholinergic neural cell. In another embodiment, the cell of the present invention is an adrenergic neural cell. In another embodiment, the cell of the present invention is a peptidergic neural cell. In another embodiment, the cell of the present invention is a sense organ or peripheral neuron supporting cell. In another embodiment, the cell of the present invention is an inner pillar cell of organ of Corti. In another embodiment, the cell of the present invention is an outer pillar cell of organ of Corti. In another embodiment, the cell of the present invention is an inner phalangeal cell of organ of Corti. In another embodiment, the cell of the present invention is an outer phalangeal cell of organ of Corti. In another embodiment, the cell of the present invention is a border cell of organ of Corti. In another embodiment, the cell of the present invention is a Hensen cell of organ of Corti. In another embodiment, the cell of the present invention is a vestibular apparatus supporting cell. In another embodiment, the cell of the present invention is a type I taste bud supporting cell. In another embodiment, the cell of the present invention is an olfactory epithelium supporting cell. In another embodiment, the cell of the present invention is a Schwann cell. In another embodiment, the cell of the present invention is a satellite cell encapsulating peripheral nerve cell bodies. In another embodiment, the cell of the present invention is an enteric glial cell.

In another embodiment, the cell of the present invention is a central nervous system neuron. In another embodiment, the cell of the present invention is a glial cell. In another embodiment, the cell of the present invention is an astrocyte. In another embodiment, the cell of the present invention is an oligodendrocyte. In another embodiment, the cell of the present invention is a spindle neuron. In another embodiment, the cell of the present invention is a lens cell. In another embodiment, the cell of the present invention is an anterior lens epithelial cell. In another embodiment, the cell of the present invention is a crystalline-containing lens fiber cell. In another embodiment, the cell of the present invention is a karan cell. In another embodiment, the cell of the present invention is a pigment cell. In another embodiment, the cell of the present invention is a melanocyte. In another embodiment, the cell of the present invention is a retinal pigmented epithelial cell.

In another embodiment, the cell of the present invention is a germ cell. In another embodiment, the cell of the present invention is an oogonium. In another embodiment, the cell of the present invention is an oocyte. In another embodiment, the cell of the present invention is a spermatid. In another embodiment, the cell of the present invention is a spermatocyte. In another embodiment, the cell of the present invention is a spermatogonium cell. In another embodiment, the cell of the present invention is a spermatozoon.

In another embodiment, the cell of the present invention is a nurse cell. In another embodiment, the cell of the present invention is an ovarian follicle cell. In another embodiment, the cell of the present invention is a sertoli cell. In another embodiment, the cell of the present invention is a thymus epithelial cell.

In another embodiment, the cell of the present invention is derived from an organ. In another embodiment, the cell of the present invention is derived from a tissue. In another embodiment, the cell of the present invention is derived from a cell line. In another embodiment, the cell of the present invention is derived from a primary cell culture. In another embodiment, the cell of the present invention is a HeLa cell. In another embodiment, the cell of the present invention is a U2OS cell.

In another embodiment, the cell of the present invention is a plant cell. In another embodiment, the cell of the present invention is an invertebrate cell. In another embodiment, the cell of the present invention is a vertebrate cell. In another embodiment, the cell of the present invention is an insect cell. In another embodiment, the cell of the present invention is an amphibian cell. In another embodiment, the cell of the present invention is a reptile cell. In another embodiment, the cell of the present invention is a mammalian cell.

In another embodiment, the methods of the present invention comprise treating a macular degeneration disease, comprising a mutated fibrillin-like extracellular matrix protein 1 (EFEMP1) gene in a subject comprising the steps of: contacting an eye cell with a recombinant serotype 2 adeno-associated virus (AAV) vector comprising a wild-type EFEMP1 transgene. In another embodiment, the methods of the present invention comprise inhibiting a macular degeneration disease, comprising a mutated fibrillin-like extracellular matrix protein 1 (EFEMP1) gene in a subject comprising the steps of: contacting an eye cell with a recombinant serotype 2 adeno-associated virus (AAV) vector comprising a wild-type EFEMP1 transgene. In another embodiment, the methods of the present invention comprise abrogating a macular degeneration disease, comprising a mutated fibrillin-like extracellular matrix protein 1 (EFEMP1) gene in a subject comprising the steps of: contacting an eye cell with a recombinant serotype 2 adeno-associated virus (AAV) vector comprising a wild-type EFEMP1 transgene. In another embodiment, the methods of the present invention comprise reversing a macular degeneration disease, comprising a mutated fibrillin-like extracellular matrix protein 1 (EFEMP1) gene in a subject comprising the steps of: contacting an eye cell with a recombinant serotype 2 adeno-associated virus (AAV) vector comprising a wild-type EFEMP1 transgene.

In another embodiment, the present invention provides that an eye cell is an eye cell comprising primary cilia. In another embodiment, the present invention provides that an eye cell is a retinal cell. In another embodiment, the present invention provides that a retinal cell is a retinal cell comprising primary cilia. In another embodiment, the present invention provides that an eye cell is a retinal pigment epithelial (RPE) cell.

In another embodiment, the methods of the present invention comprise transducing a retinal cell, comprising the step of: administering to a retinal cell a recombinant serotype 2 adeno-associated virus (AAV) vector. In another embodiment, the methods of the present invention comprise transducing a RPE cell comprising the step of: administering to a retinal cell a recombinant serotype 2 adeno-associated virus (AAV) vector. In another embodiment, the methods of the present invention comprise engineering a retinal cell, comprising the step of: administering to a retinal cell a recombinant serotype 2 adeno-associated virus (AAV) vector. In another embodiment, the methods of the present invention comprise engineering a RPE cell comprising the step of: administering to a retinal cell a recombinant serotype 2 adeno-associated virus (AAV) vector.

In another embodiment, the methods of the present invention comprise treating, abrogating, inhibiting, or reversing Malattia Leventinese (ML). In another embodiment, ML is a dominantly-inherited macular degeneration that is very similar in phenotype to age-related macular degeneration (AMD), a disease that affects a significant percentage of the elderly population in the developed world.

In another embodiment, ML is an autosomal dominant disorder characterized by the formation of deposits called drusen between the retinal pigment epithelium (RPE) and Bruch's membrane by middle age. In another embodiment, during the latter stages of the disease, pathology, such as decreased visual acuity, geographic atrophy, pigmentary changes, and choroidal neovascularization can become apparen.

In another embodiment, ML of the present invention is caused by a missense mutation (R345W) in the fibrillin-like extracellular matrix protein 1 (EFEMP1) protein. In another embodiment, the EFEMP1 protein localizes between the photoreceptors and the apical membrane of the retinal pigment epithelium (RPE) in normal individuals, and accumulates just outside of the basolateral membrane of the RPE in diseased individuals.

In another embodiment, the present invention provides that secretion of EFEMP1 protein from the RPE is normally through the apical membrane. In another embodiment, the present invention provides that secretion of EFEMP1 protein is misdirected basolaterally as a result of the R345W mutation.

In another embodiment, the present invention provides that polarized RPE cells are transduced with recombinant adeno-associated virus (rAAV) vectors expressing the wild-type and mutant EFEMP1 protein. In another embodiment, the present invention provides that polarized RPE cells are transduced in vivo with recombinant adeno-associated virus (rAAV) vectors expressing the wild-type and mutant EFEMP1 protein. In another embodiment, the present invention provides that polarized human RPE cells are transduced with recombinant adeno-associated virus (rAAV) vectors expressing the wild-type and mutant EFEMP1 protein. In another embodiment, the present invention provides that polarized human RPE cells are transduced in vivo with recombinant adeno-associated virus (rAAV) vectors expressing the wild-type and mutant EFEMP1 protein. In another embodiment, the present invention provides that polarized primary cultured human fetal RPE (hfRPE) cells are transduced with recombinant adeno-associated virus (rAAV) vectors expressing the wild-type and mutant EFEMP1 protein.

In another embodiment, the present invention provides that the ML-causing mutation in the EFEMP1 protein results in decreased levels of secretion from polarized hfRPE cells, which is due to intracellular accumulation of the mutant protein in the endoplasmic reticulum (ER). In another embodiment, the present invention provides that accumulation of misfolded protein in the ER, rather than the presence of mutant protein in the extracellular matrix, is the major factor underlying ML disease progression.

In another embodiment, the methods of the present invention comprise treating, abrogating, inhibiting, or reversing ML by administering AAV vectors of the present invention comprising the transgene EFEMP1$^{wt}$. In another embodiment, the methods of the present invention comprise treating, abrogating, inhibiting, or reversing ML by administering AAV2 vectors of the present invention comprising the transgene EFEMP1$^{wt}$. In another embodiment, the methods of the present invention comprise treating, abrogating, inhibiting, or reversing ML by administering AAV vectors of the present invention comprising the transgene EFEMP1$^{wt}$ directed by a CMV promoter.

In another embodiment, the methods of the present invention provide that treating ML with an AAV vector comprising the transgene EFEMP1$^{wt}$ results in reversed directional secretion from hfRPE cells when compared to renal epithelial cells.

In another embodiment, the methods of the present invention provide a method for transducing a cochlear cell, comprising the step of: administering to a cochlear cell a recombinant serotype 2 adeno-associated virus (AAV) vector. In another embodiment, the methods of the present invention provide a method for engineering a cochlear cell, comprising the step of: administering to a cochlear cell a recombinant serotype 2 adeno-associated virus (AAV) vector. In another embodiment, a cochlear cell of the present invention is a ciliated cochlear cell.

Experimental Details Section

Materials and Experimental Methods

Retinal Cells

Primary human fetal (15-17 weeks of gestation) RPE cells (hfRPE) were isolated from human eyes and cultured according to previous methods. Cells were removed from culture flasks by treatment with a mixture of 0.25% trypsin-ETDA and IU/ml dispase and seeded (2.0×105 cells/cm2) on to 12-mm Transwell-Clear membranes (0.4-^im pore size, Corning, Corning, N.Y.) coated with 10^xg/cm2 human extracellular matrix (BD Discovery Labware, Bedford, Mass.) according to the manufacturer's instructions. These passage 1 hfRPE cells were cultured to obtain differentiated, polarized hfRPE monolayers. Media was replaced at least twice a week. Weekly transepithelial resistance (TER) readings were measured with an EVOM ohmmeter (World Precision Instruments, Sarasota, Fla.) and normalized readings obtained for a blank Transwell-Clear membrane containing media only. Type I Madin-Darby canine kidney (MDCK) cells were provided by Joshua H. Lipschutz (Department of Medicine, University of Pennsylvania, Philadelphia, Pa.), and cultured as confluent epithelial monolayers on Transwell-Clear membranes.

Antibodies

The mouse monoclonal anti-FLAG M2, rabbit polyclonal anti-FLAG, and mouse anti-sheep Na+,K+-ATPase antibodies were all purchased from Sigma (St. Louis, Mo.). The antibody to β-actin was obtained from Santa Cruz Biotechnologies (Santa Cruz, Calif.). Mouse anti-zona occludens 1 (ZO-1) antibody was purchased from Zymed Laboratories (South San Francisco, Calif.). The mouse anti-human EMM-PRTN/CD147 (neurothelin) antibody was purchased from BD Pharmingen (San Diego, Calif.). The secondary antibodies for immunoblotting, anti-rabbit HRP and anti-mouse HRP, were purchased from Amersham Biosciences UK (Buckinghamshire, England). The secondary antibody for immunofluorescence (donkey anti-mouse Alexa 594) was purchased from Molecular Probes (Carlsbad, Calif.).

Plasmid Construction and AAV Vector Production

Human EFEMP1$^{wt}$-FLAG and EFEMP1$^{mut}$-FLAG constructs from the pKl backbone plasmid were cloned in place of the EGFP transgene in pAAV2.CMV.EGFP with NotI and BgR1 to create pAAV2.CMV.hEFEMP1$^{wt}$-FLAG and PAAV2.CMV.hEFEMP1$^{mut}$-FLAG. A plasmid containing −585 to +38 of the human vitelliform macular dystrophy 2 (VMD2) promoter (pLacF.VMD2). The VMD2 promoter, with the flanking restriction sites SpeI and NsiI created by PCR, was cloned in place of the CMV promoter in pAAV2.CMV.EGFP using the compatible restriction sites NheI and PstI to create pAAV2.VMD2.EGFP. Human EFEMP1$^{wt}$-FLAG and EFEMP1$^{mut}$-FLAG constructs from the pKl backbone plasmid were then cloned in place of the EGFP transgene using NotI and BgR1 to create pAAV2.VMD2.hEFEMP1$^{wt}$-FLAG and pAAV2.VMD2.hEFEMP1$^{mut}$-FLAG. All rAAV2/5 and 2/1 vectors were produced and titered at the Viral Vector Core at the University of Pennsylvania (Philadelphia, Pa.). AAV2 vector genomes from pAAV2.CMV.EGFP, pAAV2.CMV.hEFEMP1$^{wt}$-FLAG, and pAAV2.CMV.hEFEMP1$^{mut}$-FLAG were packaged into AAV serotype 5 capsids.

AAV2 vector genomes from pAAV2.VMD2.EGFP, pAAV2.VMD2.hEFEMP1$^{wt}$-FLAG and pAAV2.VMD2.hEFEMP1mut-FLAG were packaged into AAV serotype 1 capsids.

Transduction of Polarized Epithelial Cells

Four weeks after seeding on Transwell-Clear membranes, monolayers of hfRPE cells having a TER>200 Qcm were exposed to rAAV2/1 vectors at an MOI of 106 vector genome copies (vg)/cell in 500^l media apically for 4 days at 37° C., 5% CO2. MDCK cell monolayers were exposed to AAV2/5 vectors under the same conditions. After washing with fresh media, cells were cultured in the appropriate media, and EGFP expression was monitored at least once a week by fluorescence microscopy to determine the approximate level of expression and percentage of transduced cells.

Monitoring of hfRPE Properties

The TER of transduced hfRPE cells was monitored weekly as described. Eight weeks after transduction, cells were fixed with 4% paraformaldehyde/PBS for further analysis. Morphology and appearance was monitored by light microscopy of the monolayer. Immunofluorescence staining was performed on fixed monolayers according to previously described methods. Cells were incubated with primary antibodies to ZO-1 (1:33), Na+,K+-ATPase (1:100), and CD147/EMMPRIN (1:1000) for 1 h at 37° C. and secondary antibody (1:200) for 1 h at 37° C. Stained monolayers were fixed with 4% paraformaldehyde/phosphate-buffered saline (PBS), excised with a scalpel, and mounted on microscope slides using Vectashield mounting medium (Vector Laboratories, Inc., Burlingame, Calif.). Signal was observed using confocal fluorescence microscopy, and images in the x-y plane were captured through the entire depth (Z-axis) of a representative portion of each monolayer.

Cilia Immunostaining

MDCK cells were stained with monoclonal primary antibody against acetylated alpha tubulin (Sigma) followed by goat anti-mouse secondary antibody conjugated to FITC. Images were taken with a Nikon Eclipse E600 fluorescence microscope under ×1000 magnification. Primary cilia are highly flexible and, therefore, are not seen in the same focal plane for all cells. DAPI-stained cell nuclei are blue.

Immunoprecipitation and Immunoblotting

After transgene expression reached maximal levels as determined by EGFP fluorescence, media on transduced cells was replaced with 500 fxl of serum-free media in the apical and basal chambers, and cultured for 24-72 hours. Media from each chamber was then collected. Complete protease inhibitor cocktail (Roche Diagnostics, Mannheim, Germany) stock solution was added to a IX concentration, and the samples were frozen at −70° C. for further analyses. Cytoplasmic protein extracts were isolated by harvesting the cell monolayers in IX PBS, treating them in lysis buffer (10 mM Hepes, pH 7.6, 10 mM NaCl, 1.5 mM MgCl2, 0.2 mM EDTA, 1% Triton X-100, 20% glycerol) for 30 min on ice with IX Complete Protease Inhibitors (Roche Diagnostics, Mannheim, Germany), followed by centrifugation to pellet insoluble material. EFEMP1-FLAG was immunoprecipitated from media and cytoplasmic protein extracts with EZview Red M2 affinity beads (Sigma, St. Louis, Mo.) according to the manufacturer's instructions. Bound proteins were eluted, and separated by SDS-PAGE on 10% Bis/Tris NuPAGE gels (Invitrogen, Carlsbad, Calif.), and then transferred to nitrocellulose membranes. Aliquots of cytoplasmic protein extracts were also separated by SDS-PAGE as described as a loading control. Immunoblotting was performed using a rabbit anti-FLAG primary antibody (Sigma, St. Louis, Mo.; diluted 1:1000 in 5% non-fat dry milk/TBST) or a mouse anti-(3-actin primary antibody (Santa Cruz Biotechnologies, Santa Cruz, Calif.; diluted 1:2000) and HRP secondary antibodies diluted 1:5000 in 5% non-fat dry milk/TBST, followed by development using the ECL Plus Western Blotting Detection System (GE Healthcare UK, Buckinghamshire, UK). Chemiluminescence was detected using a Molecular Dynamics phosphoimager (GE Healthcare UK, Buckinghamshire, UK), and band intensities were quantified using ImageQuant software (GE Healthcare UK, Buckinghamshire, UK).

De-Glycosylation Assays

EFEMP1-FLAG proteins in media or in cytoplasmic protein extracts were immunoprecipitated as described, denatured by boiling in IX Glycoprotein Denaturation Buffer (New England Biolabs, Ipswich, Mass.), and either mock-treated or de-glycosylated with Endoglycosidase Hf (EndoHf, New England Biolabs, Ipswich, Mass.) or N-Glycosidase F (PNGase F or EndoF, New England Biolabs, Ipswich, Mass.) for 3 h at 37° C. according to the manufacturer's instructions. Treated and un-treated proteins were separated by SDS-PAGE and detected by immunoblotting as described above.

Statistical Analysis

TER measurements were recorded for multiple wells weekly, and each reading was normalized to a blank well containing media only. Mean values were calculated and displayed graphically, and error was calculated as the standard error of the mean (SEM). For polarized secretion analysis, bands were quantified using a phosphoimager and normalized to values recorded for negative controls (EGFP-transduced cells) on each gel. Experiments were repeated in triplicate, and mean values were displayed graphically. Error was calculated as the SEM. P values were calculated by comparing values for basal and apical secretion for each sample. For experiments comparing intracellular and extracellular protein, bands were quantified using a phosphoimager, and values were normalized to values detected for intracellular p-actin. Values detected for basolateral and apical secretion were added to compute total secreted protein, and these values were compared to intracellular protein to determine the percentage of secreted protein.

Example 1: Effects of Viral Infection and Mutant EFEMP1 Expression on HFRPE Cells In order to express EFEMP1$^{wt}$-FLAG and EFEMP1$^{mut}$-FLAG in hfRPE cells, genes encoding these fusion proteins were delivered by infecting the cells with recombinant AAV serotype 2/1 vectors (rAAV2/1). This serotype of rAAV was shown to transduce RPE cells at a high level in vivo. Using the AAV2/1.VMD2.EGFP vector, it was found that an MOI of $10^6$ vg/cell was sufficient to transduce 80-90% of RPE cells in culture. Using this MOI, we infected differentiated hfRPE cell monolayers with AAV2/1 vectors expressing EGFP, hEFEMP1$^{wt}$-FLAG, or hEFEMP1$^{mut}$-FLAG under the control an RPE-specific promoter (VMD2). Cells were maintained for 3-4 weeks prior to analysis to allow for maximal activation of the VMD2 promoter.

Figure 4D:
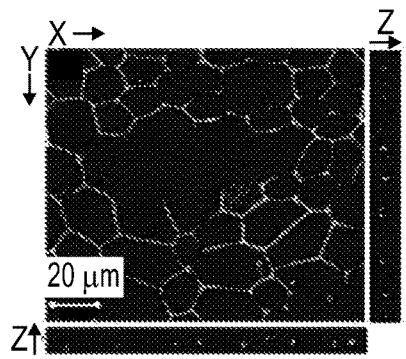
FIG. 4 shows the effects of rAAV2/1 transduction and EFEMP1-FLAG expression on hfRPE morphology and tight junction formation. A-C are immunofluorescence images of cells fixed 8 weeks following infection and stained with an antibody to ZO-1. Images were captured by 3-dimensional confocal microscopy, and are shown for each plane (x-y, x-z, and y-z). Scale bars=20 µm. D. is a graph depicts the mean TER of hfRPE cells following infection by AAV2/1 vectors. Error bars=SEM.
Figure 4D:
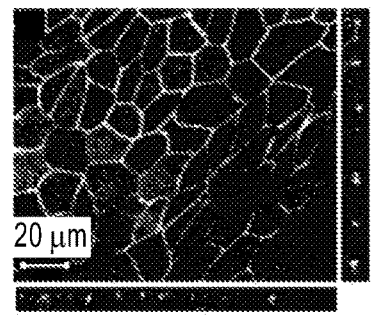
Figure 4D:
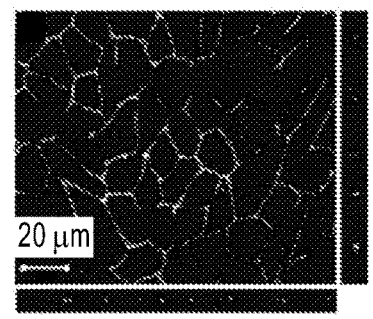
Figure 4D:
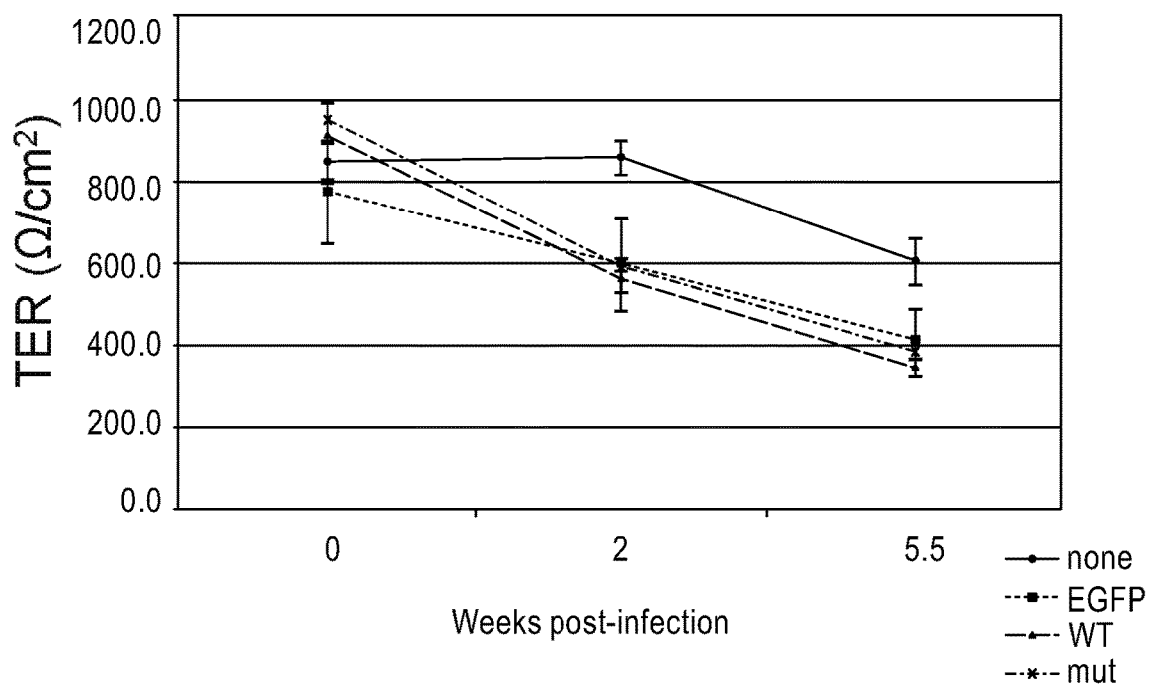

Then transduced hfRPE cells were analyzed to determine if any adverse effects of viral infection or overexpression of EFEMP1$^{mut}$ could be detected. Light microscopy after eight weeks post-infection showed that cells transduced with all three vectors displayed proper morphological characteristics of RPE cells, such as pigmentation and a cobblestone-like appearance (FIG. 4A-C). In order to determine whether virally-transduced cells maintained tight junction formation, transduced hfRPE cell monolayers were fixed and immunofluorescence for ZO-1, a marker for tight junctions, was performed. As shown in FIG. 4, three-dimensional confocal microscopy of stained monolayers indicated that cells transduced with all three vectors maintained proper localization of ZO-1 to tight junctions between the cells (FIG. 4D-F). Monolayer integrity was also monitored by weekly TER readings. Both experimental and control cells showed a small decline in TER readings as a function of time (FIG. 4G). The decline was greater in virus-treated cells, although no one vector caused a significantly greater decline when compared to the others. All cell monolayers maintained a TER greater than 200 Qcm2.

Figure 5:
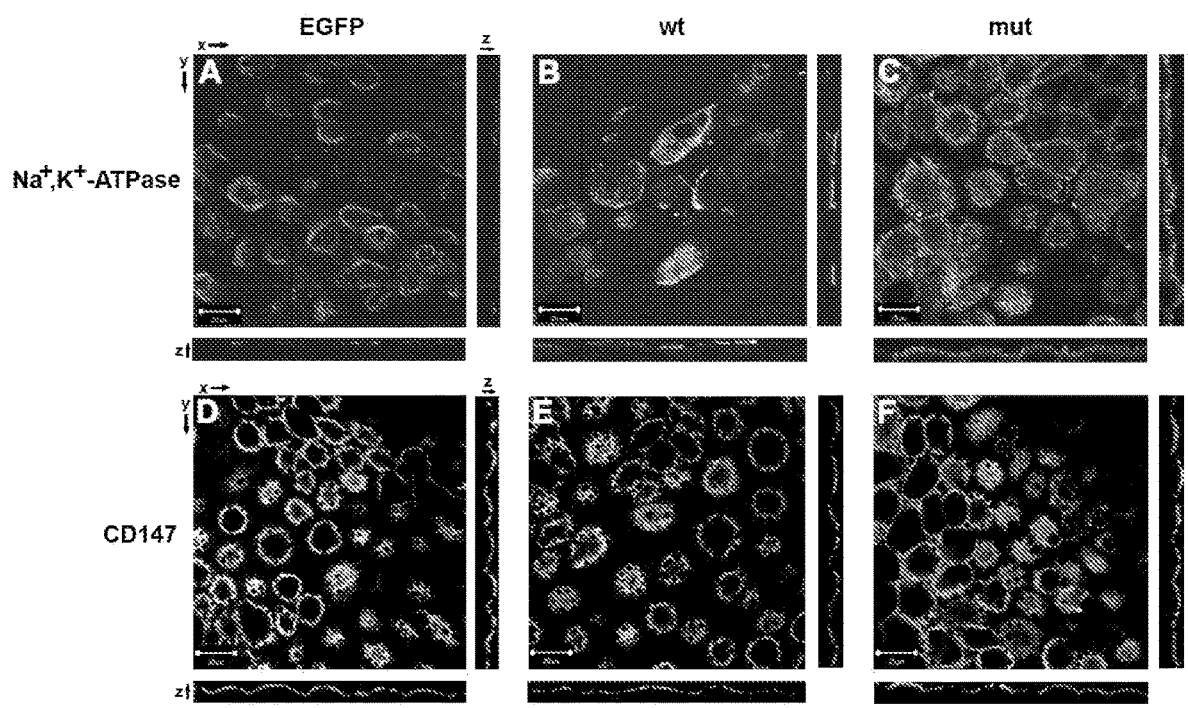
FIG. 5 depicts immunofluorescence on transduced cells performed with antibodies to Na+,K+-ATPase and EMMPRIN/CD147. Three-dimensional confocal microscopy was utilized to determine the localization of the signal. Shown are scans through three planes (x-y, x-y, and y-z). A-C show localization of Na+,K+-ATPase to the apical surface of hfRPE cells expressing each of the transgenes. D-F show localization of EMMPRIN/CD147 to the apical surface of transduced hfRPE cells. Scale bars=20 µm.

In order to test whether the transduced hfRPE cells were properly polarized, immunofluorescence for the Na$^+$,K$^+$-ATPase and EMMPRIN/CD147 was performed on fixed cell monolayers eight weeks post-infection. Both of these proteins are localized to the basolateral membrane of most polarized epithelial cells, but display reversed polarity in RPE cells, and are localized preferentially to the apical surface. Three-dimensional confocal microscopy of stained hfRPE monolayers indicated that cells expressing all three transgenes displayed both the Na$^+$,K$^+$-ATPase (FIGS. 5 A-C) and CD 147 (FIG. 5D-F) on the apical surface, indicating that viral transduction did not alter polarization in hfRPE cells. Taken together, these results indicate that while transduction in general had some effect on the TER, viral infection and in particular, expression of EFEMP1$^{mut}$-FLAG had no adverse effect on hfRPE cell morphology, tight junction formation, and epithelial cell polarization. The hfRPE cells in this study were therefore appropriate for investigating the polarity of EFEMP1 secretion.

Example 2: Establishment of HFRPE Monolayers

Figure 3:
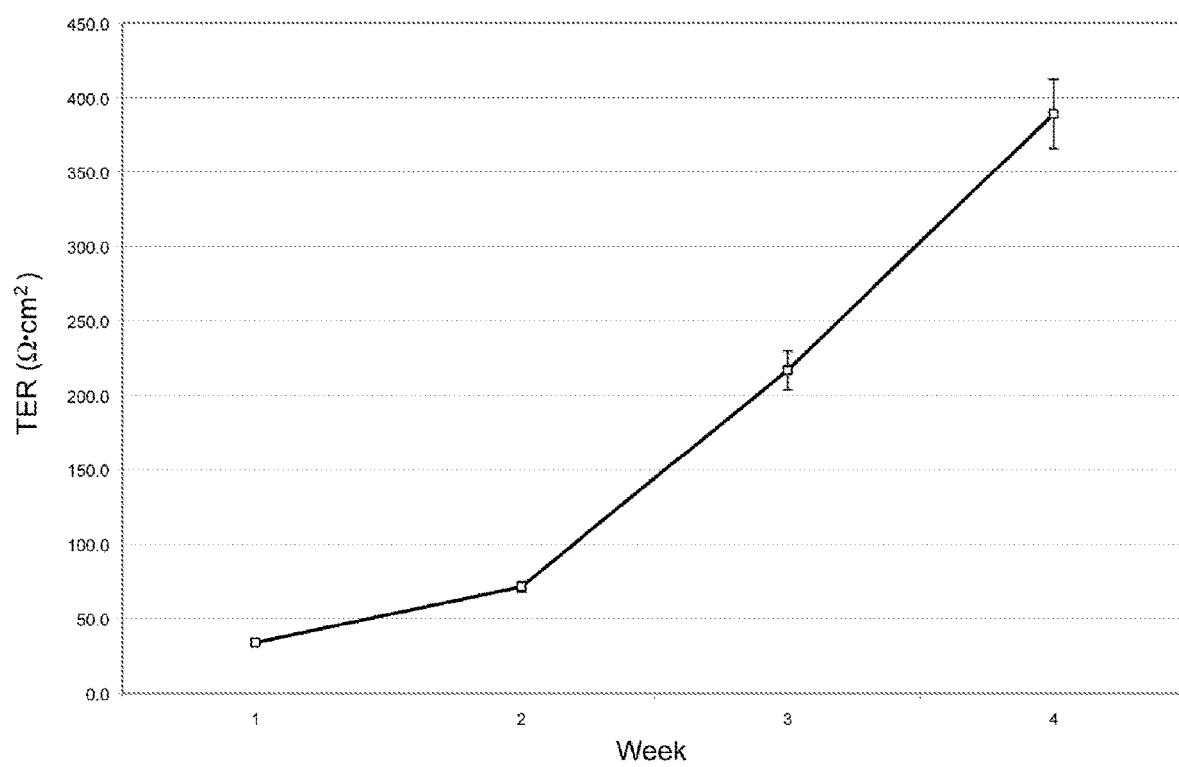
FIG. 3. Depicts Transepithelial resistance (TER) of hfRPE cells. Readings were normalized to blank Transwell filters containing media only. The graph represents mean TER readings of multiple filters through four weeks of cell culture. Error bars-SEM.

RPE cells were removed from human fetal eyes at 15-17 weeks of gestation and cultured in hfRPE growth media for at least four weeks. The cells were then removed, seeded on to Transwell-Clear membranes, and grown for another four weeks until they gained a cobblestoned appearance consistent with a differentiated epithelial cell monolayer. Pigmentation, which is markedly diminished immediately following seeding on Transwell filters, increased in these cells with time. Transepithelial resistance (TER) readings were found to increase during this time, suggesting that the monolayers had differentiated and that tight junctions had formed (FIG. 3). Monolayers with TER>200 Qcm2 are well-differentiated, as evidenced by their morphological characteristics and ATP-induced fluid transport properties, and were used for further analyses.

Example 3: Polarized Secretion of EFEMP1 by HFRPE Cells

Figure 6A:
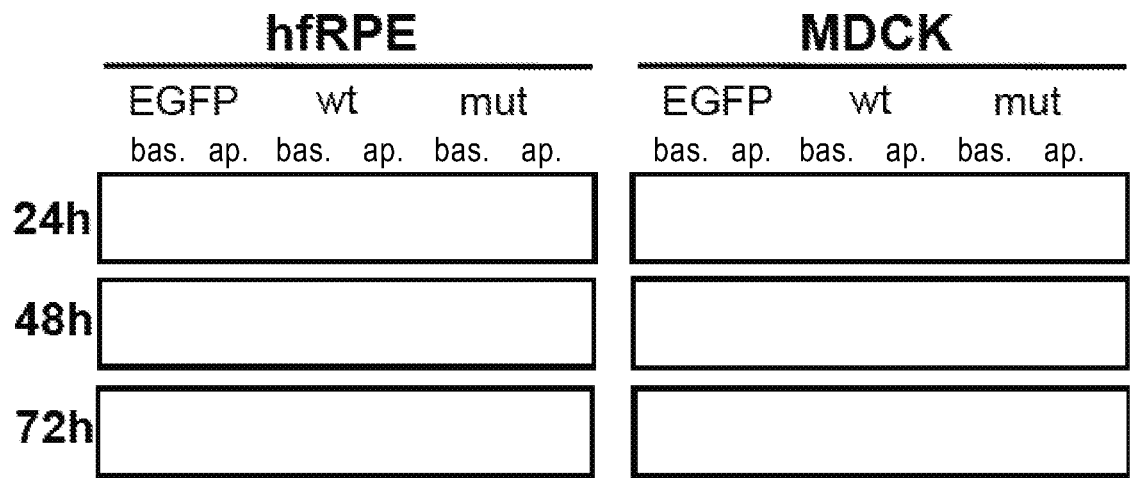
FIG. 6 shows directional secretion of EFEMP1-FLAG from polarized epithelial cells. Serum-free media was collected from apical and basolateral chambers of transduced hfRPE and MDCK cell monolayers after 24, 48, or 72 hours of incubation. EFEMP1-FLAG was immunoprecipitated from the media, separated by SDS-PAGE, and detected by immunoblotting using a polyclonal anti-FLAG antibody. A. depicts a gel showing composite of representative results from immunoprecipitation experiments. bas.=basolateral media. ap.=apical media. B. The experiment depicted in A was repeated three times, and bands detected by immunoblotting for EFEMP1-FLAG were quantified. Average percentages of secretion (basolateral or apical) are depicted graphically. P-values were calculated by comparing data sets of basal secretion (black bars) to apical secretion (grey bars) for each timepoint. Error bars=SEM.

In individuals with ML, localization of the protein is altered, and EFEMP1 resides outside the basolateral membrane of the RPE, adjacent to drusen. To test whether RPE cells secrete EFEMP1 apically, and that the R345W mutation in the protein that leads to ML misdirects this secretion basolaterally, hfRPE cell monolayers were transduced with rAAV2/1 vectors expressing EFEMP1$^{wt}$-FLAG or EFEMP1$^{mut}$-FLAG, and secretion of the proteins into the apical and basolateral media at various timepoints was analyzed. As a control epithelial cell line, MDCK cell monolayers transduced with AAV2/5 vectors expressing EGFP, EFEMP1$^{wt}$-FLAG, or EFEMP1$^{mut}$-FLAG were used. Apical and basolateral media was removed from the cells, replaced with serum-free medium, and cultured for 24-72 hours. EFEMP1-FLAG was immunoprecipitated from the media and detected by immunoblotting. As shown in FIG. 6A (left panels), contrary to our hypothesis, EFEMP1$^{wt}$-FLAG was secreted mostly into the basolateral media through 72 hours, with only some protein detected in the apical media. Interestingly, EFEMP1$^{mut}$-FLAG exhibited the same directional secretion pattern as EFEMP1$^{wt}$-FLAG in these cells, with most protein detected in the basolateral media when compared to the apical media. However, no decrease in band intensity for the secreted mutant protein was recorded (FIG. 4A, left panels), which is consistent with previous findings that the protein exhibits decreased levels of secretion.

The secretion pattern of EFEMP1 in dog kidney epithelial (MDCK) cells was different. These cells secreted EFEMP1$^{wt}$-FLAG entirely into the apical media (FIG. 6A, right panels). Similar to the results obtained herein with hfRPE cells, no reversal of directional secretion was detected for the mutant protein, and almost all secretion from MDCK cells was directed apically. These cells also appeared to secrete fewer mutants than wild-type protein (FIG. 6A, right panels).

Figure 6B:
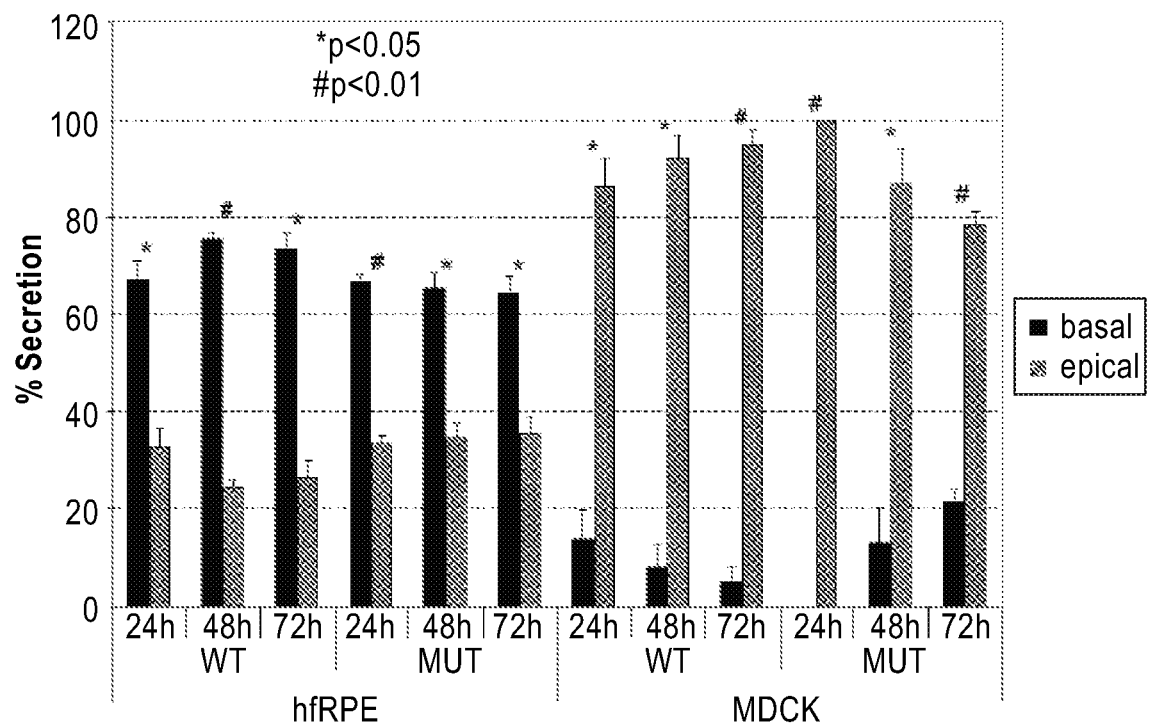

Quantification of EFEMP1 secretion from hfRPE and MDCK cells was performed using results from triplicate experiments, and is displayed graphically in FIG. 6B. More than 60% of wild-type and mutant EFEMP1-FLAG is basolaterally secreted by hfRPE cells (p<0.01 for each construct), compared to less than 25% for MDCK cells for each timepoint examined. About 40% of EFEMP1-FLAG is apically secreted by hfRPE cells, while close to 80% was apically secreted by MDCK cells. No significant difference was detected in the directional secretion of EFEMP1$^{wt}$ compared to EFEMP1$^{mut}$. Taken together, the results in FIG. 6 confirm that EFEMP1wt is basolaterally secreted by hfRPE cells, and that the disease-causing R345W mutation does not misdirect the secretion of the protein.

Figure 7:
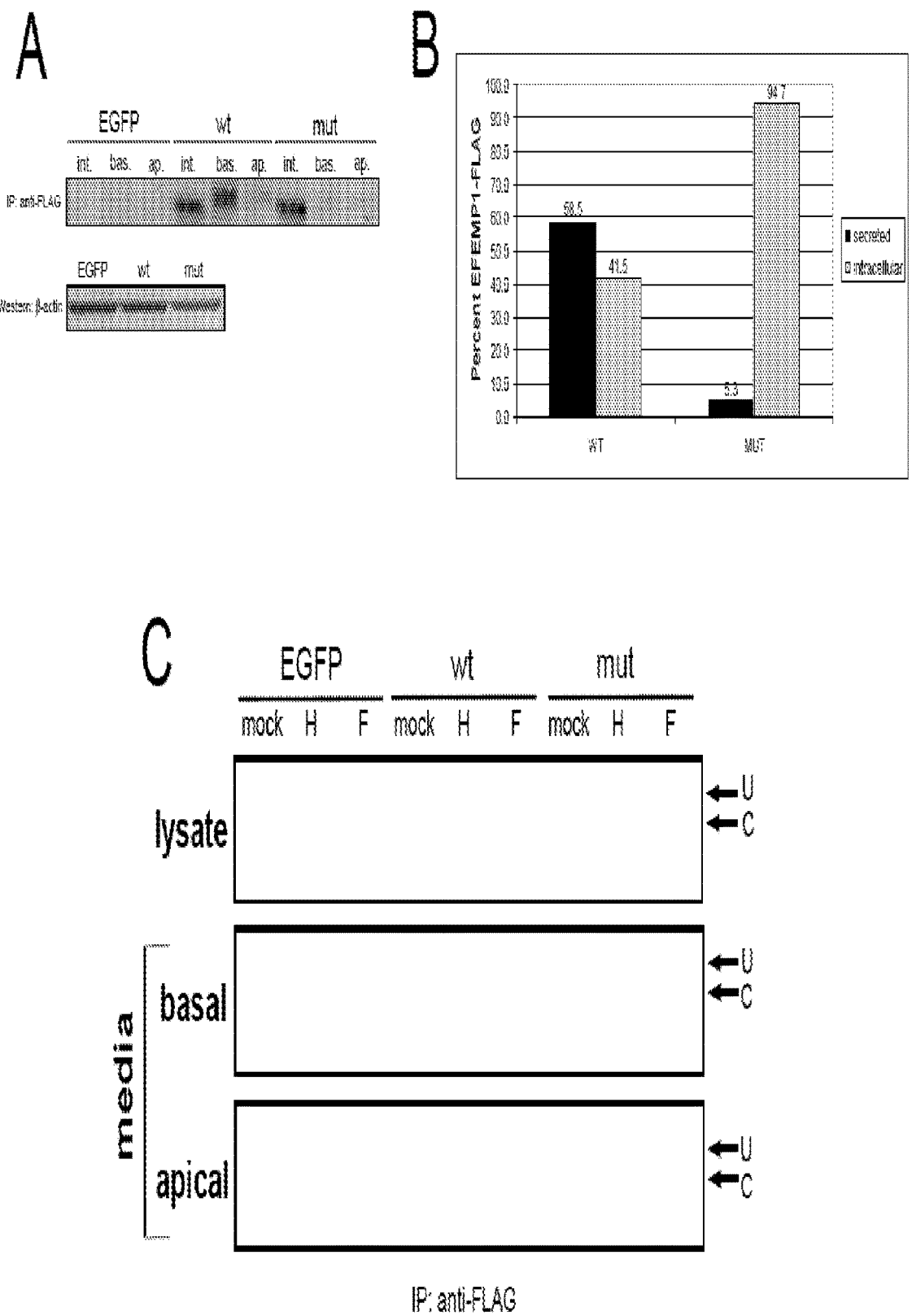
FIG. 7 shows intracellular retention of EFEMP1$^{mut}$-FLAG within the ER of polarized hfRPE cells. A. depicts a graph showing a composite image of immunoblot results from immunoprecipitation of EFEMP1-FLAG from hfRPE cell lysate and media is shown. int.=intracellular. bas.=basolateral media. ap.=apical media. (3-actin immunoblots of whole cell lysates are included as loading controls. B. Quantitative analysis of results shown in A, normalized to (3-actin. C. Results of immunoblotting for EFEMP1-FLAG following treatment with EndoHf (H) and PNGaseF (F) are shown. Uncleaved (U) forms of EFEMP1-FLAG (with covalently-linlced N-glycans) are represented by the upper arrow in each panel, while forms with cleaved glycans (C) migrate to the position indicated by the lower arrow in each panel. Faint, lower molecular weight bands below the EFEMP1-FLAG bands represent heavy-chain IgG.

Example 4: Mutant EFEMP1 is Aberrantly Secreted from HFRPE Cells and Accumulates in the ER The results outlined in FIG. 4 indicated that the protein is normally secreted in this direction by these cells, and that there is no change in the direction of secretion as a result of the R345W mutation. Next, the ability of EFEMP1$^{mut}$ to accumulate within polarized hfRPE cells was investigated. Media on transduced hfRPE cells was changed to serum-free media, and 24 hours later, media and cell lysates were harvested. EFEMP1-FLAG was then immunoprecipitated from media and cell lysates and separated by SDS-PAGE. Results of this experiment are shown in FIG. 7 A. Whereas abundant EFEMP1$^{wt}$-FLAG was detected in basolateral media, with minimal amounts detected in apical media, EFEMP1$^{mut}$-FLAG was barely detectable in both basolateral and apical media, consistent with the findings in FIG. 6A. In addition, unlike EFEMP1$^{wt}$-FLAG, most of the total mutant protein seemed to be present in the cytoplasm. Quantification of the intensity of the bands detected in FIG. 7 A revealed that close to 60% of the EFEMP1$^{wt}$-FLAG signal was present as secreted protein, but only about 5% of the mutant protein was secreted, leaving about 95% in the cytoplasm (FIG. 7B). These data show that in hfRPE cells, mutant EFEMP1 is defective in secretion and accumulates intracellularly.

In order to confirm the ER localization of the accumulated cytoplasmic EFEMP1$^{mut}$-FLAG protein in polarized hfRPE cells, the maturation state of N-linked glycosylation of the protein was measured. Processing of proteins in the ER involves the addition of high-mannose glycans, which are sequentially cleaved by the time they have has been transported to the mid-Golgi. Endoglycosidase H (EndoH) cleaves these high mannose residues specifically, and therefore is used to localize the compartmentalization of proteins in the secretory pathway. EFEMP1-FLAG was immunoprecipitated from transduced hfRPE cell lysates, apical, and basolateral media, and denatured. Immunoprecipitated proteins were treated with EndoH or PGNaseF (EndoF), a glycosidase which cleaves all N-linked glycans from proteins, and separated by SDS-PAGE. Immunoblotting shows that the intense band corresponding to EFEMP1mut-FLAG in the cell lysate is EndoH sensitive, indicating that it accumulates within the ER (FIG. 7C). EFEMP1$^{wt}$-FLAG was localized to the ER, although the band intensity was much lower than that seen for the mutant protein. This result suggests that once wild-type EFEMP1 reaches the Golgi, it is rapidly shuttled out of the cell. In contrast, both wild-type and mutant EFEMP1-FLAG secreted into either the apical and basolateral media were insensitive to EndoH, indicating proper Golgi processing (FIG. 7C). All EFEMP1 protein was EndoF-sensitive in both the lysate and the media (FIG. 7C), demonstrating that EFEMP1 remains N-glycosylated throughout its processing. The results depicted in FIG. 7 show that mutant EFEMP1 is defective in its secretion from polarized hfRPE cells, leading to accumulation of the protein within the ER.

Example 5: Transduction of Kidney Cells Via Retrograde Injection with AAVS

For retrograde delivery of AAV, mice were anesthetized and the left kidney was exposed via a 2 cm flank incision. A clamp was placed on the ureter below the injection site to prevent leakage to the bladder. The temperature of the kidney was lowered to reduce metabolic demands of this organ during the procedure. Using a 30-gauge needle, AAV particles were delivered via the ureter just below the ureteropelvic junction. The total volume of viral solution did not exceed 50 µL. After 5-15 minutes, the clamp was removed and the site was surgically closed. The tissue was then warmed back to 37° C.

AAVs carrying a reporter gene bounded by inverted terminal repeats (ITRs) from AAV serotype 2 but packaged in capsids from AAVs of other serotypes (Such a virus carrying an AAV5 capsid would be termed AAV2/5). For these studies, $10^9$ genome copies of hybrid AAVs carrying CMV.EGFP or CMV.Luciferase were delivered via retrograde injection into the kidneys of wild-type adult CD1 mice. Two to three weeks after these injections, animals were imaged for luciferase activity (FIG. 1A) or kidneys were harvested and evaluated for presence of EGFP (FIG. 1B,C).

Mice kidneys were injected, via a retrograde approach, with AAVs carrying one of two separate reporters, luciferase or enhanced green fluorescent protein (EGFP). Expression of luciferase (FIG. 1A) and EGFP (FIG. 1B,C) in the injected kidney, but not the contralateral control kidney, was extremely robust using AAV capsids of several different serotypes. AAV2/8 and AAV2/9 resulted in high levels of reporter gene expression specific to the targeted kidney; lower levels of transgene expression were detected after injection of AAV2/6 and AAV.rh8 (FIG. 1B). While a number of recombinant viruses, including lentivirus, adenovirus, and AAV serotypes 1-5 have were tested in vivo in the kidney, none of these have resulted in as efficient or as stable transduction of tubular epithelial cells as observed with the novel viruses AAV2/8 and AAV2/9. Histological evaluation revealed that EGFP was efficiently and specifically expressed in renal tubular epithelial cells in the region of the kidney exposed to the virus (FIG. 1C). There was no evidence of inflammatory/immune response relating to presence of AAV capsid antigens and/or the reporter protein. EGFP expression occurred in renal tubular epithelial cells, especially collecting duct cells, which are the cells of origin of the great majority of renal cysts (FIG. 1C).

Example 6: Imaging of Renal Primary Cilia

Figure 12:
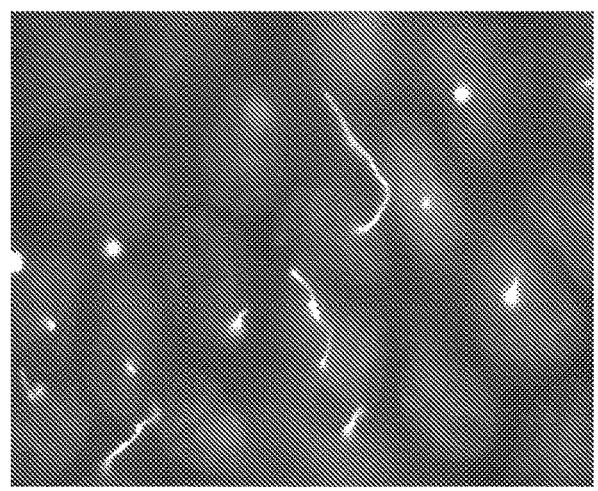
FIG. 12 depicts a micrograph (×1000) of primary renal cilia that are seen in green. DAPI-stained cell nuclei are blue.

The ability to reliably identify primary renal cilia is important for the functional and localization experiments described. The primary cilia are identified using immunfluorescence microscopy and antibody against acetylated alpha tubulin (FIG. 12).

Example 7: AAV Efficiently Transduces Renal Collecting Duct Cells In Vitro

Figure 2:
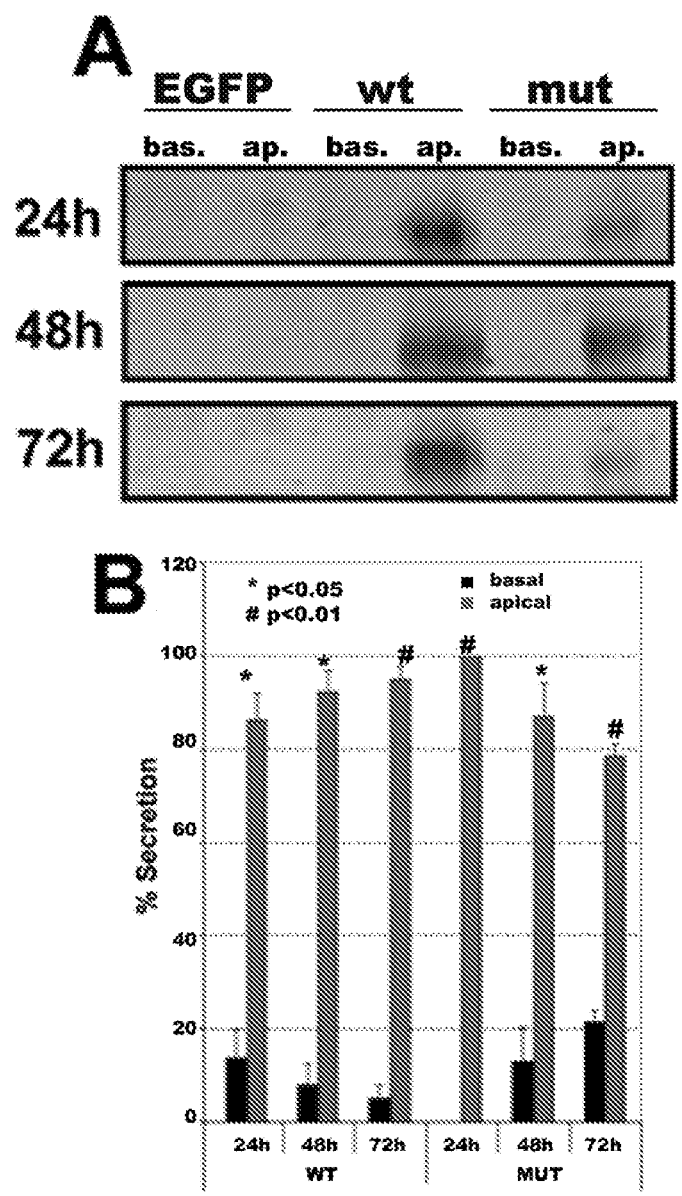
FIG. 2 shows the transduction of polarized MDCK cells with AAV2/5.EFEMP1-FLAG. (A) Depicts a Western Blot gel of FLAG-tagged EGF-containing fibrillin-like extracellular matrix protein 1 (EFEMP1): AAV2/5.EFEMP1-wt or AAV2/5.EFEMP1-mut. Directional (apical; ap) secretion of both wt and mut EFEMP1 of basal (bas) and apical (ap) media for 72 hours. (B) Depicts a bar graph quantifying the amount of protein detected in (A).

AAV2/5 efficiently transduced MDCK Strain I cells, which are of collecting duct origin, and transgenic proteins undergo the predicted cellular processing (FIG. 2). Thus, efficient transduction of a renal collecting duct cell line in vitro with AAV was successfully preformed (FIG. 2).

Example 8: Optimizing Conditions to Target Renal Collecting Duct Cells In Vitro

Because the great majority of cysts originate in the collecting ducts, AAV particles, generated through transient transfection of the human 293 cell line and then verified for purity and titered are delivered to cultured collecting duct cells, e.g. iMCD3. These cells are cultured as confluent epithelial monolayers on Transwell filters. Once the cells have differentiated (5-7 days following plating), the efficiency of transduction is compared after infection using a panel of 30 novel AAVs. Infections are performed in triplicate using an identical dose of virus ($5 \times 10^9$ genome copies) per well of cells. The chicken p-actin promoter (and CMV enhancer; CpA) drive readily detectable levels of expression in these cells. Once the optimal vector is identified, additional studies identify the optimal pH for transduction. Since the pH of urine can vary significantly in wild-type mice, this information is important for determining optimal in vivo delivery conditions. In vitro expression levels are further manipulated through dose optimization and/or incorporation of renal tubular epithelial cell-specific promoters. The transgene is an EGFP-luciferase fusion cDNA.

The initial analysis is a master spreadsheet in which the measured properties are tabulated for each of the serotypes. Since AAV binding to cellular receptors and endocytosis can occur within 60 milliseconds, clearance by urine flow is not an obstacle (FIG. 1).

The results identify the conditions and serotype that allow for the highest and most stable protein expression in renal tubular epithelial cells in vitro and then in vivo.

A series of studies are performed to evaluate the four optimal (lead) rAAV vectors from for testing of transduction of renal tubular epithelial cells in vivo. For these, retrograde ureteral injections (one injection per mouse) are performed in four-week old wild-type mice. Each virus is injected through the ureter in cohorts of 5 mice. The dose is $1 \times 10^9$ genome copies. Volumes are held constant at 50 µl and result in exposure of 1/8 to 1/2 of the kidney to virus. Kidney luciferase luminescence and EGFP fluorescence is evaluated quantitatively in the living mouse two weeks after treatment using the Xenogen MS system. EGFP is then measured qualitatively in tissue sections derived from the treated mice. The animal is imaged for luciferase activity at weekly intervals for four weeks, and then kidneys are harvested and evaluated for presence of EGFP. Tissue is evaluated for identification of transduced cells and evaluation of the relative efficiency of transduction of specific cell populations as a function of distance from the ureter/renal pelvis. Histological and immunohistochemical evaluation are used to examine the presence (and nature) of any potential inflammatory response.

The identification of the optimal AAV viral subtype and conditions for infection of renal tubular epithelial cells in vivo is preformed. Cell hypertrophy accounts for much of the increase in kidney size in the postnatal period. Since most of the cell division that accounts for the increase in kidney size during development occurs in mid-to-late gestation there is no significant dilution in transgene expression of the postnatally-treated cells due to mitosis. The cell division that persists after birth is predominantly in the duct tips at the periphery of the kidney, therefore, dilutional effects are present only in those areas.

Example 9: Generation of AAV Encoding Polycystin-2 and Ift88

Figure 8:
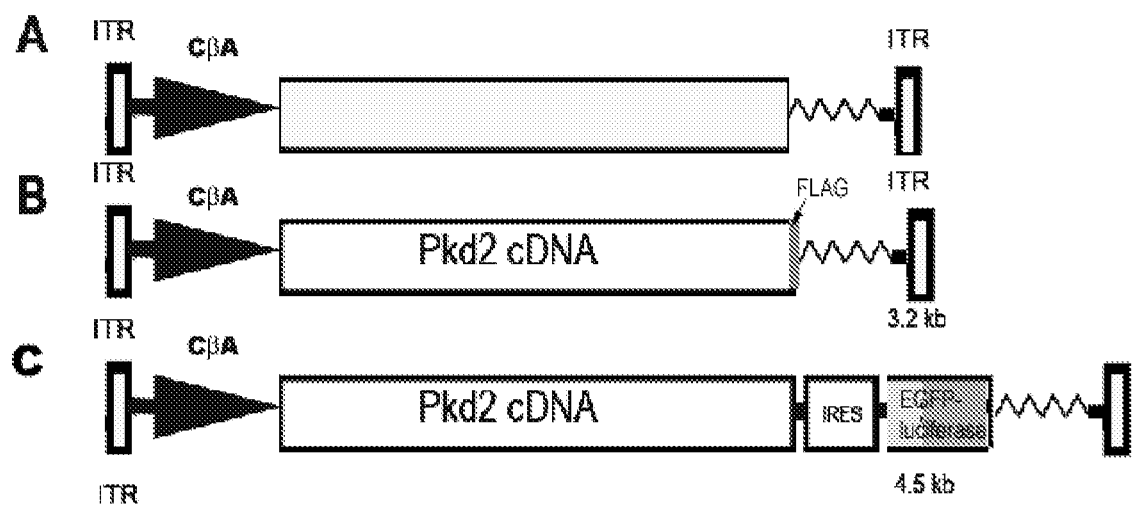
FIG. 8 depicts a schematic representation of pkd2 containing transgene cassettes. Prototype Pkd2-containing transgene cassettes without (A) and with (B, C) tags. The FLAG tag is fused to the Pkd2 cDNA in (B) and an IRES element connects the EGFP-luciferase fusion protein in (C). C3A=chicken beta actin promoter/enhancer; ITR, inverted terminal repeat; IRES=internal ribosome entry site. Note that all constructs fit within the cargo limitations of AAV2/2 (4.8 kb).
Figure 9:
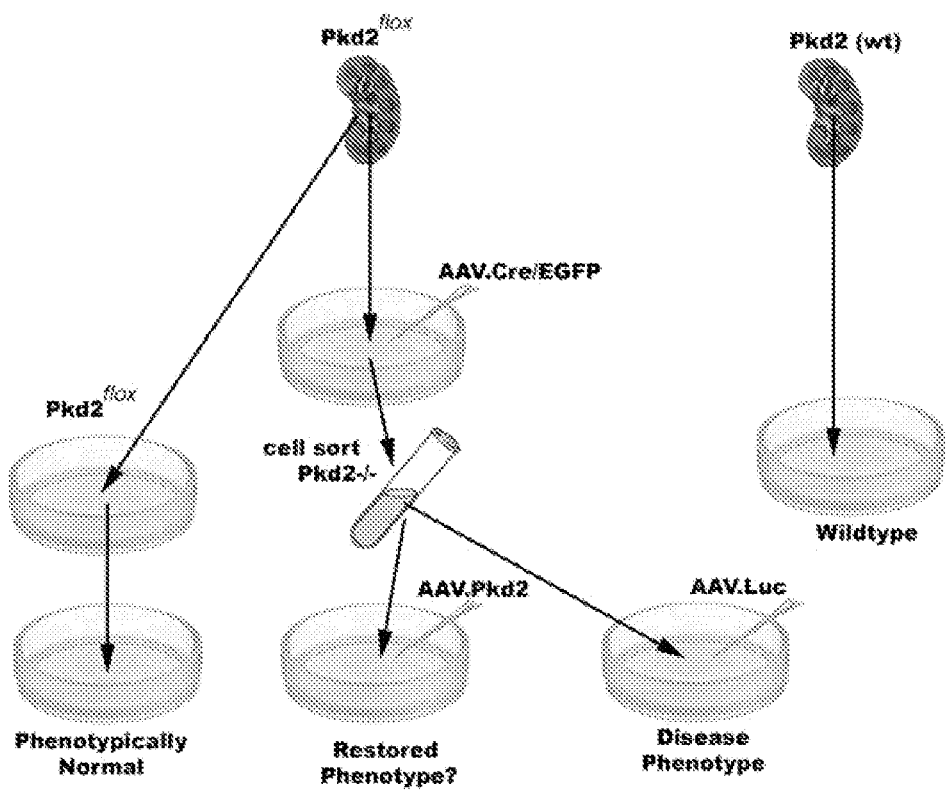
FIG. 9 depicts a scheme for evaluation of ciliary rescue in vitro in Pkd2-deficient renal collecting duct cells. Renal collecting duct cells are isolated from Pkd2"ox mice. These cells are phenotypically normal until exposed to Cre. After infection of these cells with AAV.Cre/EGFP, cell sorting for the EGFP tag ensures a pure population of Pkd2-deficient cells (Pkd2−/−). Half of these cells are exposed to the experimental vector, AAV.Pdk2 and the other half is exposed to a control vector (AAV.Luc). Polycystin-2 is then be localized and calcium responses measured in the experimental and control cells. Cells from a wild-type kidney are used as a positive control. Note: both tagged and untagged AAV.Pkd2 are generated. For simplicity, this figure assumes that the tagged version is suffice for rescue.
Figure 10:
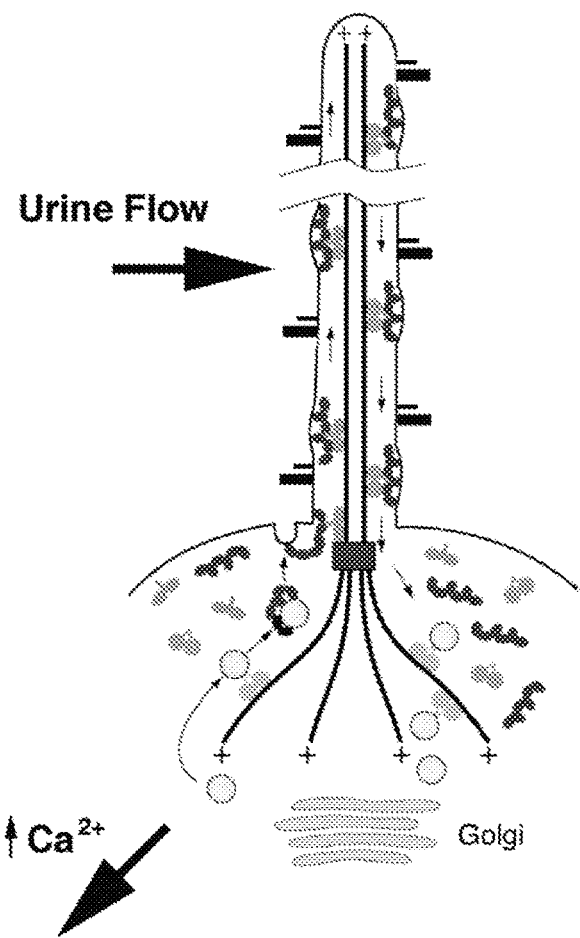
FIG. 10 depicts a scheme of the Renal Primary Cilium. Multiple proteins involved in PKD are localized to the primary renal cilium, including the intraflagellar transport (IFT) particle, Ift88 (gray), which is necessary for cilia formation, and polycystin-2 (black bar), which is necessary for cilia function.

Similar methods are used to generate AAVs containing wild-type Pkd2 or Ift88, though for simplicity, the description below is just for Pkd2. The chicken p-actin (CpA) regulatory sequence in pAAV.CBA.EGFP-Luciferase is replaced with the Pkd2 cDNA, provided, and with the Ift88 cDNA, provided. These cDNAs fall well within the cargo capacity of AAV, with Pkd2 being 2,904 bp and Ift88 being 2,472 bp in length. There is no need to introduce an epitope as polycystin-2 antibody is readily available (e.g. from Zymed Inc.); however, as this will facilitate the studies, both FLAG-tagged and untagged Pkd2 cDNA are generated. The untagged construct controls for any alteration of function that could potentially result from presence of the FLAG tag, though this is unlikely as the FLAG tag does not alter function or distribution of an AAV-delivered transgene. To allow for imaging and quantification of the Pkd2 transgene expression in vivo, the cDNAs for fluorescent reporter proteins (EGFP-luciferase) is incorporated into additional plasmids. These are generated separately to control for potential toxicity caused by over-expression of EGFP-luciferase in vivo. These fluorescent sequences are linked via internal ribosome entry site (FIG. 8).

Robust expression of two reporters in kidney tubular epithelial cells in vivo was viewed especially with serotype AAV2/9 (FIG. 1).

Example 10: pkd2$^{ws2s/ws183}$ is an Animal Model for ADPKD

Figure 11:
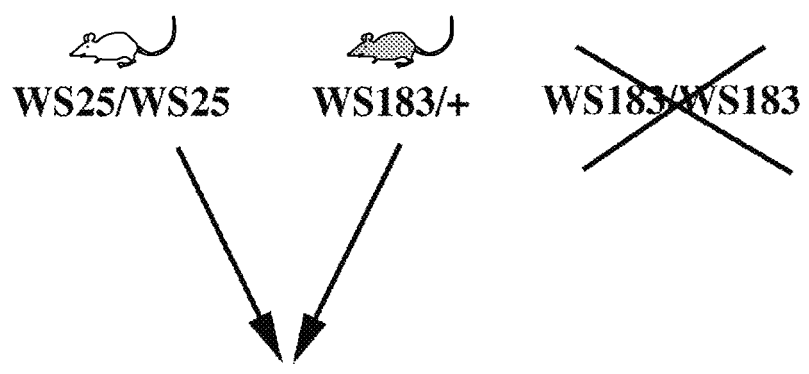
FIG. 11 Mating strategy. Pkd2$^{WS183/WS183}$ mice have two null alleles and die shortly after birth of severe cystic renal disease. Pkd2$^{WS183/+}$ and Pkd2$^{WS25/WS25}$ mice are viable and can be bred.

Loss of heterozygosity involves a null, or non-functional, allele with a subsequent somatic mutation. The murine Pkd2$^{WS25/WS183}$ model is double heterozygote that faithfully mimics loss of heterozygosity and human ADPKD. In this model, the WS183 allele (FIG. 11), which has a deletion of exon 1, is a true null allele, while the WS25 allele, also containing a deletion of exon 1, is unstable and undergoes intragenic recombination. In essence, this results in accelerated loss of heterozygosity. By 11 weeks, all Pkd2$^{WS25/WS183}$ mice display severe cystic renal disease that is indistinguishable from that described for human disease. The mating strategy is shown in FIG. 11. An AAV vector containing the WT allele is used for gene therapy to rescue the cystic WS25/WS183 phenotype of Pkd2$^{WS25/WS183}$ mice.

Example 11: Ift88 Knockout Emryo as an Ex-Vivo Model for ADPKD

Mutation of the intraflagellar transport 88 (Ift88) gene causes the pathogenesis of polycystic kidney and is a model of ADPKD. In these animals, homozygotic mutation of the Ift88 gene results in a complex phenotype that included polycystic kidneys, portal fibrosis, pancreatic acinar cell atrophy, midline cleft palate, and preaxial polydactyly. Ift88 knockout mice are embryonic lethal, and are noted to have both situs inversus and neural tube defects at embryonic day 9.5-10.5. In mice homozygous for the Ift88 gene knockout, the ventral node cells lack cilia on their apical surface. The loss of cilia on these cells leads to defects in right-left patterning caused by an abnormal nodal flow of morphogens. As noted previously, Pkd2 homozygous knockout mice also display situs inversus. The product of the Ift88 gene is Ift88 protein, also known as polaris because of the various polarity related defects associated with the different alleles of ift88 gene. Rescue of the abnormal stunted cilia is preformed in ift88 mutant cortical collecting duct cell line using an AAV vector containing a transgene encoding the wild type ift88.

Example 12: Isolation of Primary Renal Cilia

Figure 13:
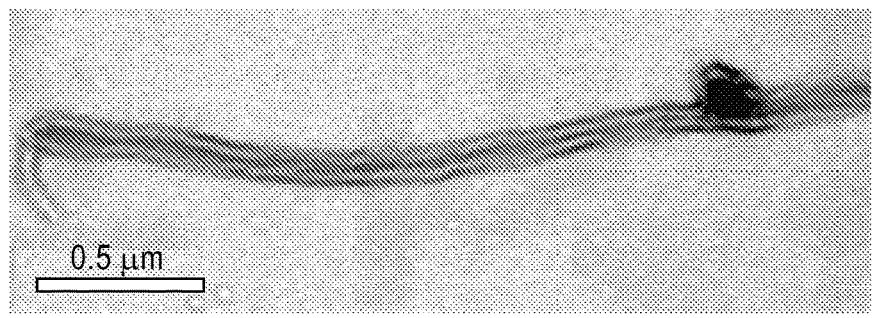
FIG. 13 depicts a micrograph of an isolated primary renal cilia on a FEI Tecnai transmission electron microscope (11,000×).

In order to examine the function of primary cilia following rescue, isolation of primary renal cilia was preformed. Briefly, MDCK cells were grown to confluence and the cells were deciliated with a high calcium solution. A series of high-speed centrifugations were then performed using a sucrose cushion and primary renal cilia were isolated. The pellet was re-suspended and fixed in 2% glutaraldehyde, loaded on a Formvar coated grid, subjected to "negative" staining with 2% aqueous uranyl acetate, and viewed on a FEI Tecnai transmission electron microscope (FIG. 13).

Example 13: Protein Localization Using Electron Gold Immunolabeling

Figure 14:
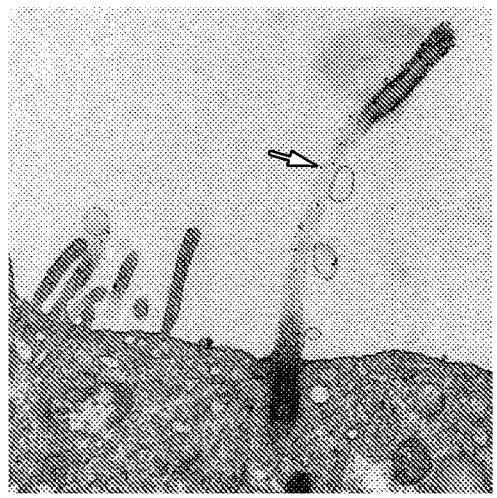
FIG. 14 depicts an electron gold localization of exocyst Sec10 to the Primary Cilium. The image was taken on a FEI Tecnai transmission electron microscope (×53,400 magnification).

Localization of polycystin-2 to the primary cilia following rescue confirms that gene therapy has worked. Detailed imaging of fixed cells was performed using electron microscopy and antibody against the myc epitope tag in MDCK cells stably expressing exocyst Sec10-myc. Sec10-myc expressing MDCK cells were grown on Transwell filters for 7 days. Pre-embedding immunolabeling was performed. Mouse anti-myc antibody was used at 1:200 dilution to identify the myc epitope present on Sec10, as antibody to Sec10 is not available to us. Secondary goat anti-mouse antibody was tagged with ultrasmall gold (Aurion). The gold label was further enhanced with silver staining for 25 minutes and formed black dots on the image (arrow). FIG. 14 demonstrates Sec10-myc localization to the primary renal cilium. Localize of polycystin-2 to the primary cilia is preformed in a similar manner. The image was taken on a FEI Tecnai transmission electron microscope (×53,400 magnification).

Example 14: Measurement of Calcium Influx in Response to Flow

A non-fluorescent, $CO_2$-independent medium for Fura-2 calcium imaging containing: 1.26 mM $CaCl_2$), 0.81 mM MgSO4, 5.37 mM KCL, 0.44 mM KH2PO4, 137 mM NaCl, 0.34 mM Na2HPO4, 5.55 mM D-glucose, 2.0 mM L-glutamine, 1.0 mM sodium pyruvate, 20.0 mM HEPES buffer, and 1% bovine serum albumin.

Briefly, the collecting duct cells from Pkd2WS25/WS183 mouse kidneys, both untreated and treated with AAV encoding wild-type polycystin-2, are incubated for 30 minutes at 37° C. with the calcium sensitive probe Fura-2-AM (5 μM), washed three times to remove the excess Fura-2, and placed in a GlycoTech perfusion chamber. The chamber is placed under a Nikon microscope equipped with a CCD camera, that capture paired Fura images every 5 seconds at excitation wavelengths of 340 nm and 389 nm. After equilibration for 10 minutes in the imaging medium described above, stimulation the primary cilia is preformed using a shear stress of 0.75 dynes/cm2. As controls for these studies isolated collecting duct cells from wild-type mice are grown and measurements of calcium influx in response to flow in both the presence and absence of polycystin-2 antibody are preformed.

Example 15: Isolation of Renal Primary Cilia for Measurement of Calcium Current by Patch Clamp Collecting duct cells from Pkd2$^{WS25/WS183}$ mouse kidneys treated with AAV encoding wild-type polycystin-2, are obtained as described. A second round of fluorescence activated cell sorting is performed to isolate just the collecting duct cells infected with AAV encoding, for example, polcystin-2 tagged with a red fluorescent protein, such as mCherry. Once the rescued collecting duct cells are isolated, the deciliating protocol is preformed. Briefly, the cells are suspended in a high calcium "deciliation buffer" containing 112 mM NaCl, 3.4 mM KCl, 2.4 mM NaHCO$_3$, 2 mM HEPES and 10 mM CaCl2, pH 7.0. High calcium causes centrin, the ciliary calcium binding protein, to contract forcefully and severs the cilium from the cell. Resuspended cells are shaken vigorously in this solution at 4° C. for 10 minutes, which facilitates the deciliation process. Sucrose gradient centrifugation is utilized to purify the ciliary sample (i.e. to separate it from the cellular debris). A 45% sucrose solution is prepared and placed into centrifuge tubes. The ciliary sample is loaded on top of the sucrose cushion and centrifuged at 4° C., ×10,000 g (at 27,500 rpm with Beckman SW28 rotor) for 100 minutes. The ciliary sample is collected on top of the sucrose cushion and carefully transferred into a clean centrifuge tube. The collected sample is diluted in PBS (1:10 volume ratio) and centrifuged again at 4° C., ×10,000 g for 60 minutes. The cilia, which forming the pellet, is resuspended in PBS with 2.0 mM EGTA and 0.5 mM sucrose, pH 7.0 and stored at −80° C. Twenty-five ml of solution are collected during each step and are used in Western blot for trouble-shooting and to confirm purity.

The techniques for patch clamp: the patch pipette contains a solution with 140 mM NaCl, 5.0 mM KCl, 1.0 mM MgCl2, 2.5 CaCl2), 10 mM HEPES and N-methylglucamine, pH 7.4. The signal is filtered at 5 KHz and manual adjustment of the baseline is performed.

What is claimed is:

1. An in vivo method for transducing a human retinal pigment epithelial (RPE) cell having a mutated fibrillin-like extracellular matrix protein 1 (EFEMP1) gene comprising the step of administering subretinally a recombinant adeno-associated virus (AAV) vector comprising a capsid from an AAV of serotype AAV1, AAV2, AAV5, AAV8, or AAV9; and a wild-type EFEMP1 transgene, wherein the human RPE cell is transduced and the human RPE cell expresses a wild-type EFEMP1 gene.

2. The method of claim 1, wherein said capsid is from an AAV of serotype AAV2.

3. The method of claim 1, wherein said transgene is bounded by inverted terminal repeats (ITRs).

4. The method of claim 3, wherein said ITRs are of serotype 2 AAV.

5. The method of claim 1, wherein said transgene is under the control of an RPE specific promoter.

6. The method of claim 5, wherein the RPE-specific promoter is the human vitelliform macular dystrophy 2 (VMD2) promoter.

7. The method of claim 1, wherein said cell forms tight junctions with neighboring cells and forms a layer of cells having a transepithelial resistance (TER) of >200 Ω/cm$^2$.

8. The method of claim 1, wherein said transgene encodes a protein secreted from the cell apically.

9. The method of claim 1, wherein said transgene encodes a protein secreted from the cell basolaterally.

10. The method of claim 1, wherein said cell is a polarized RPE cell.

11. The method of claim 1, wherein said cell is a pigmented RPE cell.

12. The method of claim 3, wherein said ITRs are from an AAV of a serotype other than serotype 2.

13. The method of claim 2, wherein said AAV vector comprises inverted terminal repeats (ITRs) from an AAV of a serotype other than serotype 2.

14. The method of claim 2, wherein said AAV vector comprises inverted terminal repeats (ITRs) from an AAV of serotype 2.

15. The method of claim 1, wherein administering the AAV vector comprises administering by injection.

16. The method of claim 1, wherein the transgene encodes a secreted protein.

17. The method of claim 1, wherein the method comprises detecting transduced RPE cells.

18. The method of claim 17, wherein the detecting comprises detecting fluorescence.

19. The method of claim 1, wherein a population of human RPE cells are contacted with the recombinant AAV, wherein 80%-90% of the human RPE cells are transduced.

20. An in vitro method for transducing a human retinal pigment epithelial (RPE) cell having a mutated fibrillin-like extracellular matrix protein 1 (EFEMP1) gene comprising the steps of:
   (a) providing a human RPE cell having a mutated EFEMP1 gene; and
   (b) contacting said RPE cell with a recombinant adeno-associated virus (AAV) vector comprising comprising a capsid from an AAV of serotype AAV1, AAV2, AAV5, AAV8, or AAV9; and a wild-type EFEMP1 transgene, wherein the human retinal pigment epithelial cell is transduced and the human RPE cell expresses a wild-type EFEMP1 gene.

21. The method of claim 20, wherein said capsid is from an AAV of serotype AAV2.

22. The method of claim 20, wherein said transgene is bounded by inverted terminal repeats (ITRs).

23. The method of claim 22, wherein said ITRs are of serotype 2 AAV.

24. The method of claim 20, wherein said transgene is under the control of an RPE specific promoter.

25. The method of claim 24, wherein the RPE-specific promoter is the human vitelliform macular dystrophy 2 (VMD2) promoter.

26. The method of claim 20, wherein said cell forms tight junctions with neighboring cells and forms a layer of cells having a transepithelial resistance (TER) of >200 Ω/cm$^2$.

27. The method of claim 20, wherein said transgene encodes a protein secreted from the cell apically.

28. The method of claim 20, wherein said transgene encodes a protein secreted from the cell basolaterally.

29. The method of claim 20, wherein said cell is a polarized RPE cell.

30. The method of claim 20, wherein said cell is a pigmented RPE cell.

31. The method of claim 22, wherein said ITRs are from an AAV of a serotype other than serotype 2.

32. The method of claim 21, wherein said AAV vector comprises inverted terminal repeats (ITRs) from an AAV of a serotype other than serotype 2.

33. The method of claim 21, wherein said AAV vector comprises inverted terminal repeats (ITRs) from an AAV of serotype 2.

34. The method of claim 20, wherein contacting the cell comprises administering the AAV vector comprises administering by injection.

35. The method of claim 20, wherein the transgene encodes a secreted protein.

36. The method of claim 20, wherein the method comprises detecting transduced RPE cells.

37. The method of claim 36, wherein the detecting comprises detecting fluorescence.

38. The method of claim 20, wherein a population of human RPE cells are contacted with the recombinant AAV, wherein 80%-90% of the human RPE cells are transduced.

* * * * *